United States Patent
Horii et al.

(10) Patent No.: US 8,882,683 B2
(45) Date of Patent: Nov. 11, 2014

(54) PHYSIOLOGICAL SOUND EXAMINATION DEVICE AND PHYSIOLOGICAL SOUND EXAMINATION METHOD

(75) Inventors: Noriaki Horii, Kyoto (JP); Maki Yamada, Kanagawa (JP); Chizu Habukawa, Wakayama (JP); Katsumi Murakami, Osaka (JP); Yukio Nagasaka, Osaka (JP)

(73) Assignee: Panasonic Corporation, Osaka (JP)

( * ) Notice: Subject to any disclaimer, the term of this patent is extended or adjusted under 35 U.S.C. 154(b) by 254 days.

(21) Appl. No.: 13/520,208

(22) PCT Filed: Nov. 4, 2011

(86) PCT No.: PCT/JP2011/006165
§ 371 (c)(1),
(2), (4) Date: Jul. 2, 2012

(87) PCT Pub. No.: WO2012/060107
PCT Pub. Date: May 10, 2012

(65) Prior Publication Data
US 2012/0283598 A1 Nov. 8, 2012

(30) Foreign Application Priority Data
Nov. 4, 2010 (JP) .................................. 2010-247952

(51) Int. Cl.
| A61B 7/00 | (2006.01) |
| A61B 5/08 | (2006.01) |
| A61B 5/085 | (2006.01) |
| A61B 7/02 | (2006.01) |
| A61B 5/087 | (2006.01) |
| A61B 5/00 | (2006.01) |
| A61B 7/04 | (2006.01) |

(52) U.S. Cl.
CPC ............... *A61B 7/003* (2013.01); *A61B 5/0816* (2013.01); *A61B 7/00* (2013.01); *A61B 5/085* (2013.01); *A61B 5/08* (2013.01); *A61B 7/026* (2013.01); *A61B 5/087* (2013.01); *A61B 5/7257* (2013.01); *A61B 7/04* (2013.01); *A61B 2562/0204* (2013.01)

USPC ............................................. 600/586

(58) Field of Classification Search
CPC ............ A61B 7/00; A61B 7/04; A61B 7/026; A61B 7/003; A61B 5/08; A61B 5/0816; A61B 5/085
USPC ............................................. 600/586
See application file for complete search history.

(56) References Cited

U.S. PATENT DOCUMENTS

| 6,443,907 B1 | 9/2002 | Mansy et al. |
| 7,347,824 B2 | 3/2008 | Wilkinson et al. |

(Continued)

FOREIGN PATENT DOCUMENTS

| JP | 2003-530940 | 10/2003 |
| JP | 2004-512066 | 4/2004 |

(Continued)

OTHER PUBLICATIONS

International Search Report issued Jan. 17, 2012 in International (PCT) Application No. PCT/JP2011/006165.

*Primary Examiner* — Devin Henson
(74) *Attorney, Agent, or Firm* — Wenderoth, Lind & Ponack, L.L.P.

(57) ABSTRACT

A physiological sound examination device which supports estimation of a state of a living body includes a first physiological sound measurement unit; a second physiological sound measurement unit; a power ratio calculation unit which calculates a power ratio which is a ratio of first physiological sound signal power to second physiological sound signal power; and an illness-related gain calculation unit which calculates a transfer-characteristic of the physiological sound in the living body by computing the power ratio. A power calculation unit which calculates first power which is the second physiological sound signal power in a first frequency band; and an illness-related high frequency power ratio calculation unit which calculates a sound-source-characteristic of the physiological sound by computing the first power. The computing is performed to reduce an influence of the respiratory flow velocity and/or the size of the living body.

22 Claims, 35 Drawing Sheets

(56) References Cited

U.S. PATENT DOCUMENTS

| | | |
|---|---|---|
| 7,708,697 B2 | 5/2010 | Wilkinson et al. |
| 7,850,618 B2 | 12/2010 | Wilkinson et al. |
| 7,981,045 B2 | 7/2011 | Suzuki et al. |
| 2003/0018276 A1 | 1/2003 | Mansy et al. |
| 2003/0120182 A1 | 6/2003 | Wilkinson et al. |
| 2005/0033144 A1 | 2/2005 | Wada |
| 2006/0037615 A1 | 2/2006 | Wilkinson et al. |
| 2006/0070623 A1 | 4/2006 | Wilkinson et al. |
| 2006/0100666 A1 | 5/2006 | Wilkinson et al. |
| 2007/0010722 A1 | 1/2007 | Suzuki et al. |
| 2008/0154145 A1 | 6/2008 | Wilkinson et al. |
| 2011/0092857 A1 | 4/2011 | Herscovici-Cohen et al. |

FOREIGN PATENT DOCUMENTS

| | | |
|---|---|---|
| JP | 3604127 | 12/2004 |
| JP | 2005-027751 | 2/2005 |
| JP | 2007-014501 | 1/2007 |
| JP | 2011-522582 | 8/2011 |
| WO | 01/80741 | 11/2001 |
| WO | 02/30280 | 4/2002 |
| WO | 2004/002317 | 1/2004 |
| WO | 2005/117702 | 12/2005 |
| WO | 2006/099670 | 9/2006 |
| WO | 2006/119543 | 11/2006 |
| WO | 2006/129517 | 12/2006 |
| WO | 2009/144721 | 12/2009 |

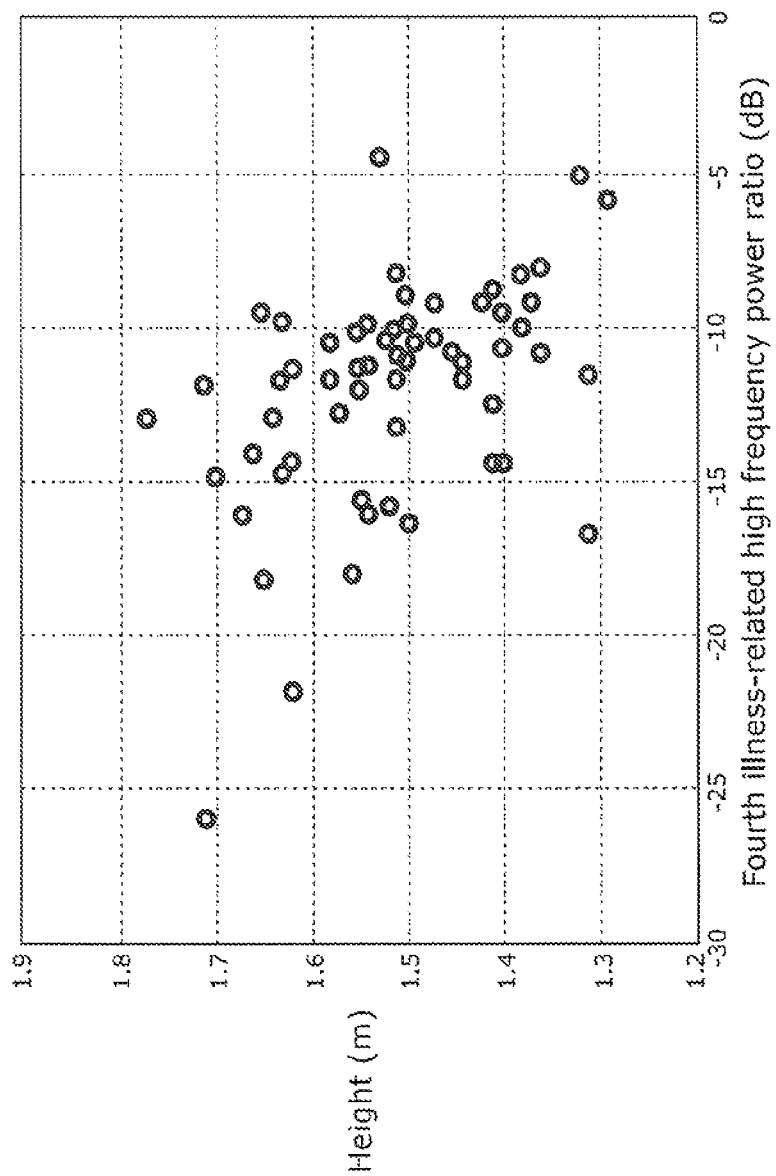

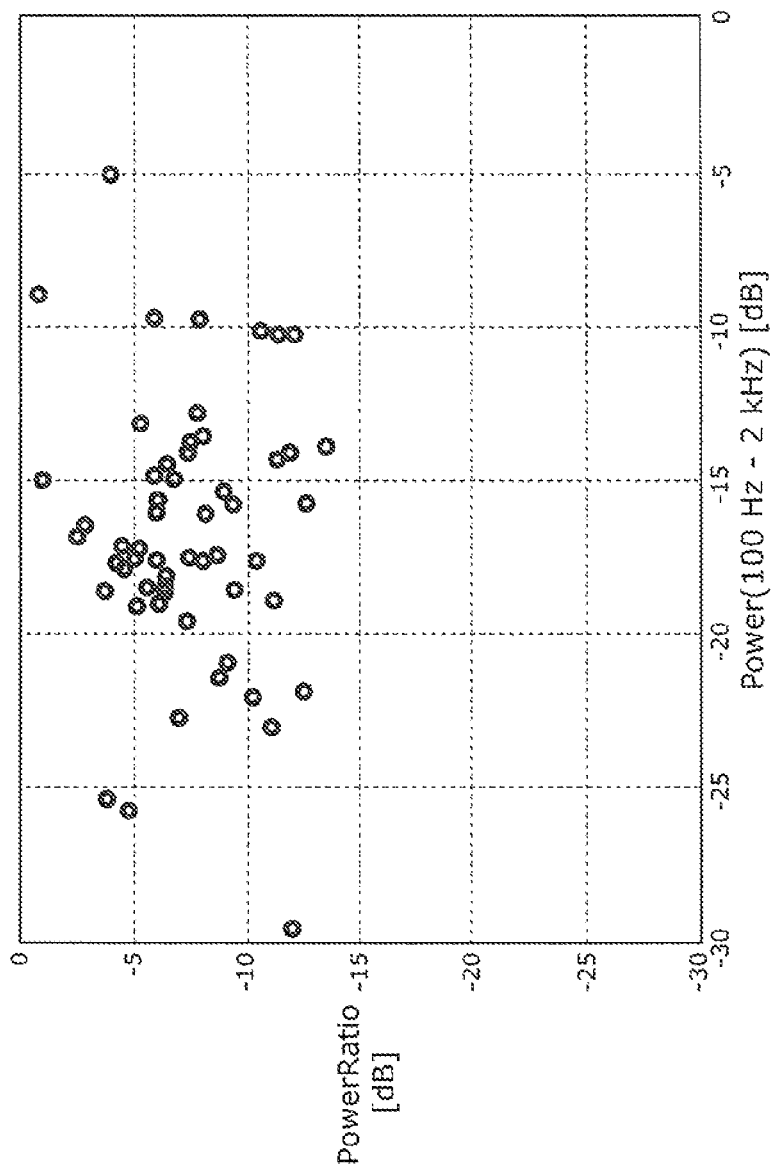

PHYSIOLOGICAL SOUND EXAMINATION DEVICE AND PHYSIOLOGICAL SOUND EXAMINATION METHOD

BACKGROUND OF INVENTION

1. Technical Field

The present invention relates to physiological sound examination devices. The present invention particularly relates to a physiological sound examination device which supports estimation of a state of a living body by measuring a physiological sound that propagates through the living body and calculating plural physiological sound characteristics.

2. Background Art

In a hospital or the like, a doctor listens to a physiological sound of a patient, such as heart sound or lung sound, using a stethoscope to make a diagnosis. The diagnosis by auscultation is based on a subjective evaluation of the doctor. On this account, skill is required to make a correct diagnosis.

The lung sound refers to all sounds, except for sounds coming from the cardiovascular system, generated by the motion of breathing in the lung and thorax regardless of whether normal or abnormal. Moreover, the lung sound is divided into a breath sound and an adventitious sound. The breath sound refers to a physiological sound whose source is airflow occurring in the respiratory tract by breathing. The adventitious sound refers to an abnormal sound, such as wheezing or pleural friction rub, caused in a pathological state. The sound source of breathing is thought to be generated in the respiratory tract which is relatively large.

In the conventional diagnosis, a diagnosis support for lung diseases is provided by performing signal processing of a lung sound. In the diagnosis support for lung diseases, an adventitious sound is detected to estimate a state of the disease. However, an objective index for the disease has not yet been established.

Pneumothorax is one of lung diseases. Pneumothorax is an air space formed between the lung and the chest wall, and appears as a decrease in breath sound intensity in physical presentation. A method of detecting a state of pneumothorax has been disclosed (see PTL 1, for example). More specifically, in this method, a sound wave is emitted by a speaker into the mouth and the trachea so that the emitted sound wave propagates through the body of the patient, and then the propagated sound wave is measured on the chest wall for signal processing. According to PTL 1, the state of pneumothorax is detected by calculating a transfer characteristic from the sound wave to be emitted and the sound wave measured on the chest wall.

Moreover, as a method without emitting a sound wave by a speaker, a method of analyzing the lung sound measured on the chest wall is disclosed (see PTL 1, for example). According to PTL 1, frequency conversion is performed using a lung sound signal measured on the chest wall, and an energy ratio between a low frequency band component and a high frequency band component is calculated. In this way, a respiratory state can be detected.

Here, for making a respiratory diagnosis, the doctor listens to the lung sound by placing a stethoscope on different positions of the body. A device which includes, in order to detect a measurement position of the lung sound, an acceleration sensor in a sensor for measuring the lung sound has been disclosed (see PTL 2, for example). According to PTL 2, output values of the acceleration sensor are integrated to calculate a moving distance of the sensor, so that the measurement position of the lung sound can be automatically detected.

Furthermore, when a patient is in a remote area, a person other than the doctor places a microphone on a predetermined position of the body of the patient to measure the physiological sound and then transmits the measured physiological sound via a communication line to the doctor who thus listens to the physiological sound signal to make a diagnosis. In order for the doctor in a remote area to be able to make a diagnosis even when the microphone is not placed on the predetermined position of the body of the patient, a device whereby more than one microphones are placed on the body of the patient to help the doctor make the diagnosis has been disclosed (see PTL 3, for example). According to PTL 3, a weighted sum is calculated using acoustic signals received from the microphones, so as to simulate an acoustic signal corresponding to a position where no microphone is placed. In this way, a diagnosis made in a remote area is supported.

CITATION LIST

Patent Literature

[PTL 1] Japanese Unexamined Patent Application Publication No. 2004-512066
[PTL 2] Japanese Unexamined Patent Application Publication No. 2005-27751
[PTL 3] Japanese Patent No. 3604127

SUMMARY OF INVENTION

However, there is a problem that the state of the disease cannot be estimated with high accuracy from the transfer characteristic of the lung sound. Even when the adventitious sound is not included, the state of the lung varies depending on the state of the disease. For example, when a patient has asthma, the state of the lungs, namely, lung parenchyma or a surface of respiratory tract, varies every day even when the patient is not being suffered from an attack and no adventitious sound such as wheezing is occurring. Accordingly, the problem exists that the state of the disease cannot be estimated with high accuracy even though the transfer characteristic of the lung is calculated using, for example, the method disclosed in PTL 1. This is because the state of the surface of the respiratory tract cannot be evaluated based only on the transfer characteristic of the lung.

In addition, though evaluation of the transfer characteristic of the lung is important in estimating the state of the disease, there is a problem that it is almost impossible to obtain only the transfer characteristic of the lung with high accuracy. This is because it is almost impossible to observe only the lung sound. When the doctor tries to observe the lung sound on the chest wall, vibration that is not from the lung sound propagates through and spreads on the chest wall through the thorax, or sound outside of the subject's body is mixed into and observed with the lung sound. For example, when the transfer characteristic of the lung is obtained by putting sound wave from the oral cavity as in PTL 1, the sound wave may propagate onto the chest wall through the thorax and the sound wave put from the oral cavity may propagate through the air to be mixed into the sensor. Therefore, it is almost impossible to evaluate the transfer characteristic of only the lung with high accuracy.

The present invention is conceived to solve the above problems and has an object to provide a physiological sound examination device and the like which obtains a physiological sound and estimates, with high accuracy, a state of a living body based on the obtained physiological sound.

In order to solve the above problems, the physiological sound examination device according to an aspect of the present invention is a physiological sound examination device which supports estimation of a state of a living body by measuring a physiological sound which propagates through the living body and calculating plural physiological sound characteristics. The physiological sound examination device includes: a first physiological sound measurement unit which measures the physiological sound in a first portion of the living body and generates a first physiological sound signal; a second physiological sound measurement unit which measures the physiological sound in a second portion of the living body and generates a second physiological sound signal, the second portion being closer to a sound source of the physiological sound than the first portion; a power ratio calculation unit which calculates a power ratio which is a ratio of power of the first physiological sound signal to power of the second physiological sound signal; a transfer characteristic index calculation unit which calculates, as one of the physiological sound characteristics, a transfer characteristic index of the physiological sound in the living body by performing a computation on the power ratio so that an influence of at least one of a respiratory flow velocity of the living body and a size of the living body is reduced; a power calculation unit which calculates first power which is power of the second physiological sound signal in a first frequency band; and a sound source characteristic index calculation unit which calculates, as an other one of the physiological sound characteristics, a sound source characteristic index of the physiological sound by performing a computation on the first power so that an influence of at least one of the respiratory flow velocity of the living body and the size of the living body is reduced.

With this configuration, by obtaining and analyzing the physiological sound in two positions of the living body, the sound source characteristic index (illness-related high frequency power ratio) and the transfer characteristic index (illness-related gain) are calculated with reduced influence of the respiratory flow velocity and the body size of the subject. Accordingly, the state of the living body can be estimated with high accuracy.

Furthermore, preferably, the power calculation unit calculates second power which is power of the second physiological sound signal in a second frequency band which is different from the first frequency band, the physiological sound examination device further includes a reference power calculation unit which calculates a first power reference value that is a value obtained by reducing the influence of difference in sizes of the living bodies included in the second power, and the sound source characteristic index calculation unit which performs the computation by calculating a ratio of the first power to the first power reference value, to calculate the sound source characteristic index.

With this configuration, the influence of the body size included in the second physiological sound signal can be reduced. Therefore, even in a case where the second power (low frequency power) varies depending on the body size of the subject, the influence of the variation can be reduced.

Furthermore, preferably, the second frequency band includes a frequency lower than a frequency in the first frequency band.

With this configuration, a first power reference value (high frequency power reference value) corresponding to the second power (low frequency power) can be set, whereby the influence of variation in the second power (low frequency power) can be reduced.

Furthermore, preferably, the power ratio calculation unit calculates the power ratio in a third frequency band and the power ratio in a fourth frequency band which includes a frequency lower than a frequency in the third frequency band, and the transfer characteristic index calculation unit calculates, as the transfer characteristic index, a ratio of the power ratio in the third frequency band to the power ratio in the fourth frequency band.

With this configuration, it is not required to set a gain reference value in advance, and the gain reference value can be calculated from the measured physiological sound.

Furthermore, preferably, the power ratio calculation unit calculates the power ratio in the third frequency band, and the transfer characteristic index calculation unit calculates a gain reference value, and calculates a ratio of the power ratio in the third frequency band to the gain reference value as the transfer characteristic index, the gain reference value being calculated using (i) at least one of a height, an age, a weight, a gender, a body surface area, and a body mass index, of the living body and (ii) a first gain prediction formula that is set in advance.

With this configuration, a gain reference value that is dependent on the physical characteristic of the subject to be measured can be set, whereby the influence of the difference among individuals in the analysis result of the state of the living body can be decreased.

Furthermore, preferably, the physiological sound examination device includes a state estimation unit which estimates whether the living body is in a good state or a bad state based on identification information set in advance, the calculated sound source characteristic index, and the calculated transfer characteristic index.

Furthermore, preferably, the state estimation unit performs the estimation using a discrimination function as the identification information. In the estimation, the living body is estimated to be in one of the good state and the bad state when a value of the discrimination function is greater than or equal to a predetermined value, and the living body is estimated to be in the other of the good state and the bad state when the value of the discrimination function is smaller than the predetermined value, when the sound source characteristic index and the transfer characteristic index are substituted into the discrimination function.

Furthermore, preferably, the state estimation unit changes a sensitivity and a specificity by selectively increasing and decreasing the predetermined value, and the sensitivity is a rate that a living body truly in the bad state is determined to be in the bad state, and the specificity is a rate that a living body truly in the good state is determined to be in the good state, in the estimation.

With this configuration, the state of the living body can be estimated, whereby even a non-expert can easily grasp whether the living body is in the good state or the bad state.

Furthermore, preferably, the state estimation unit estimates the state of the living body using a support vector machine as the identification information.

With this configuration, the state of the living body can be identified automatically and with high accuracy.

Furthermore, preferably, the state estimation unit further estimates the state of the living body from medication information related to medication for the living body.

With this configuration, the state estimation of the living body can be changed based on the content of the medication information of the living body, whereby the state estimation can be adjusted to meet a state of individual.

Furthermore, preferably, the physiological sound examination device further includes a display unit which displays an examination result including a two-dimensional map having two axes, one of the axes indicating the sound source characteristic index and the other indicating the transfer characteristic index, and the two-dimensional map being divided into plural areas by at least one border line.

With this configuration, a relationship between an area on the two-dimensional map that is used as a guide for the state and an analysis result of the physiological sound are displayed visually, whereby it is easier to understand whether the state is good or bad, and the degree of goodness or badness.

Furthermore, preferably, the two-dimensional map is divided into three by lines or curves in a direction of the axis indicating the transfer characteristic index, and into two by at least one of a line and a curve in a direction of the axis indicating the sound source characteristic index.

With this configuration, the relationship between an area on the two-dimensional map that is used as a guide for the state and an analysis result of the physiological sound are displayed visually, whereby it is easier to understand whether the state is good or bad, and the degree of goodness or badness.

Furthermore, preferably, the physiological sound examination device further includes a state estimation unit which performs estimation on whether the living body is in a good state or a bad state based on identification information set in advance, the measured sound source characteristic index, and the measured transfer characteristic index, and the state estimation unit estimates using the border line as the identification information and based on the area, in the two-dimensional map, including coordinates corresponding to the calculated sound source characteristic index and the calculated transfer characteristic index.

With this configuration, the border line for the state estimation is displayed on the two-dimensional map, whereby the estimation result of the state can be displayed in a manner that is easy to visually understand.

Furthermore, preferably, the state estimation unit estimates the state of the living body from (i) an area including the coordinates corresponding to the transfer characteristic index and the sound source characteristic index at a first time and (ii) an area including the coordinates corresponding to the transfer characteristic index and the sound source characteristic index at a second time that is different from the first time.

With this configuration, even when the illness-related high frequency power ratio and the illness-related gain have a correlation, it is possible to estimate whether the state is good or bad and the tendency based on time-series variation in the analysis result of one person.

Furthermore, preferably, the second portion is a predetermined portion in a chest or a neck, and the first portion is a predetermined portion in the chest.

With this configuration, the physiological sound propagating in the lung can be measured, whereby the state of the lung can be estimated.

Furthermore, preferably, the first portion is at a sternal notch and the second portion is at a second intercostal space on the right midclavicular line.

With this configuration, the lung sound can be measured at a position closer to the sound source of the lung sound and a position at the periphery of the lung, whereby the state of the lung can be estimated with high accuracy.

Furthermore, preferably, the second portion is closer to the neck than the first portion.

With this configuration, the lung sound can be measured at two points on a path through which the lung sound propagates within the lung, whereby the state of the lung can be estimated.

Furthermore, preferably, the state of the living body is the state of the asthmatic lungs.

With this configuration, the state of the asthmatic lungs can be determined by analyzing the lung sound.

Furthermore, a physiological sound examination method according to an aspect of the present invention is a physiological sound examination method of supporting estimation of a state of a living body by measuring a physiological sound which propagates through the living body and calculating plural physiological sound characteristics. The physiological sound examination method includes: measuring the physiological sound in a first portion of the living body and generating a first physiological sound signal; measuring the physiological sound in a second portion of the living body and generating a second physiological sound signal, the second portion being closer to a sound source of the physiological sound than the first portion; calculating a power ratio which is a ratio of power of the first physiological sound signal to power of the second physiological sound signal; calculating, as one of the physiological sound characteristics, a transfer characteristic index of the physiological sound in the living body by performing a computation on the power ratio so that an influence of at least one of a respiratory flow velocity of the living body and a size of the living body is reduced; calculating first power which is power of the second physiological sound signal in a first frequency band; and calculating, as an other one of the physiological sound characteristics, a sound source characteristic index of the physiological sound by performing a computation on the first power so that an influence of at least one of the respiratory flow velocity of the living body and the size of the living body is reduced.

With this method, the advantageous effects as provided in the above physiological sound examination device can be provided.

Furthermore, the present invention can be achieved as a program for causing a computer to execute each of the steps included in the physiological sound examination method. Such a program may be distributed via a recording medium such as a CD-ROM (Compact Disc Read Only Memory) or a transmission medium such as the Internet.

With the present invention, the physiological sound examination device can easily quantify a state of a living body from plural points of view, by analyzing a lung sound.

BRIEF DESCRIPTION OF DRAWINGS

FIG. 25B is a scatter diagram showing an example of a relationship between the illness-related high frequency power ratio and height.

FIG. 27B is a scatter diagram showing another example of the relationship between the all-band power and the illness-related high frequency power ratio, of the physiological sound.

DETAILED DESCRIPTION OF INVENTION

Figure 1:
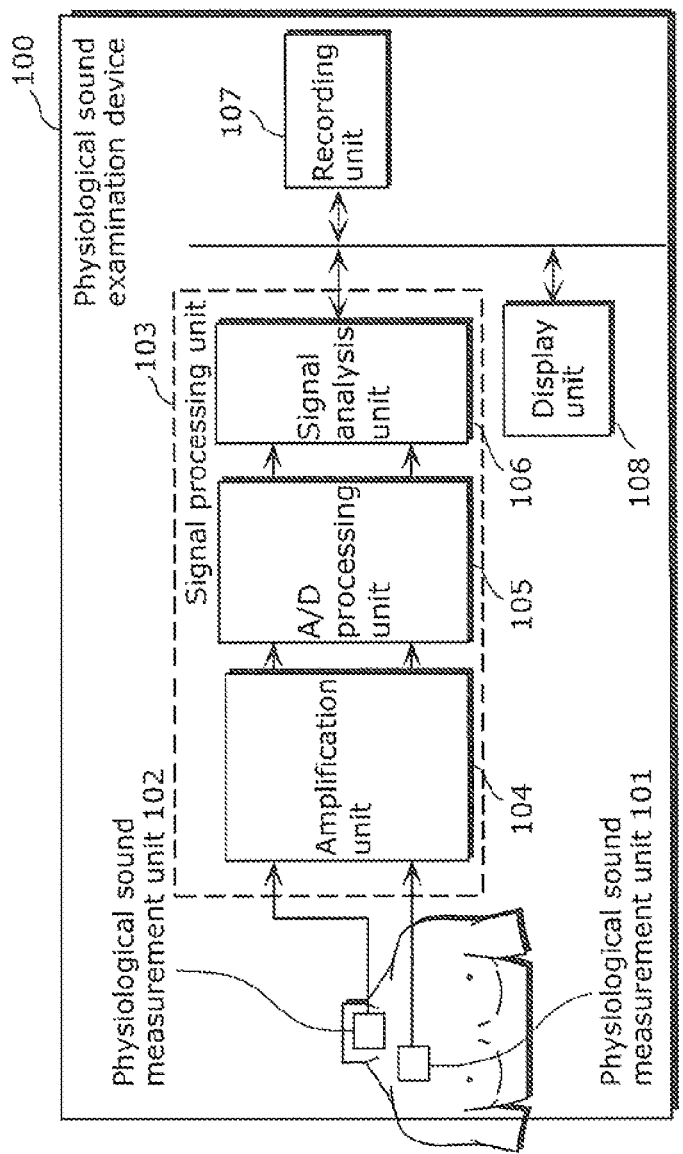
FIG. 1 shows a functional block configuration of a physiological sound examination device according to Embodiment 1.

The following describes embodiments of the present invention with reference to the drawings. It is to be noted that each of the embodiments described below is a preferable specific example of the present invention. Numeric values, shapes, materials, constituents, positions and topologies of the constituents, steps, an order of the steps, and the like in the following embodiments are an example of the present invention, and it should therefore not be construed that the present invention is determined by these embodiments. The present invention is determined only by the statement in Claims. Accordingly, out of the constituents in the following embodiments, the constituents not stated in the independent claims describing the broadest concept of the present invention are not necessary for achieving the object of the present invention and are described as constituents in a more preferable embodiment.

The same constituents are designated by the same reference numerals and are not described in some cases.

[Embodiment 1]

What is described in the present embodiment is a configuration for and method of measuring a physiological sound, generating a physiological sound signal, and calculating an illness-related high frequency power ratio and an illness-related gain from the generated physiological sound signal, of the physiological sound measurement unit.

FIG. 1 shows a functional block configuration of a physiological sound examination device 100 according to Embodiment 1.

The physiological sound examination device 100 includes: physiological sound measurement units 101 and 102 each measures a physiological sound, a signal processing unit 103, a recording unit 107 which records information and analysis result of the physiological sound signal used by the signal processing unit 103, and a display unit 108 which displays the analysis result of the physiological sound signal to the measurer. The signal processing unit 103 includes: an amplification unit 104 which amplifies each of the physiological sound signal measured by the physiological sound measurement unit 101 and the physiological sound signal measured by the physiological sound measurement unit 102; an A/D processing unit 105 which digitizes (converts into digital data) each of the physiological sound signals amplified by the amplification unit 104; and a signal analysis unit 106 which analyzes each of the physiological sound signals converted into digital data by the A/D processing unit 105. The recording unit 107 and the display unit 108 may be in an external device connected via a communication line.

Figure 2:
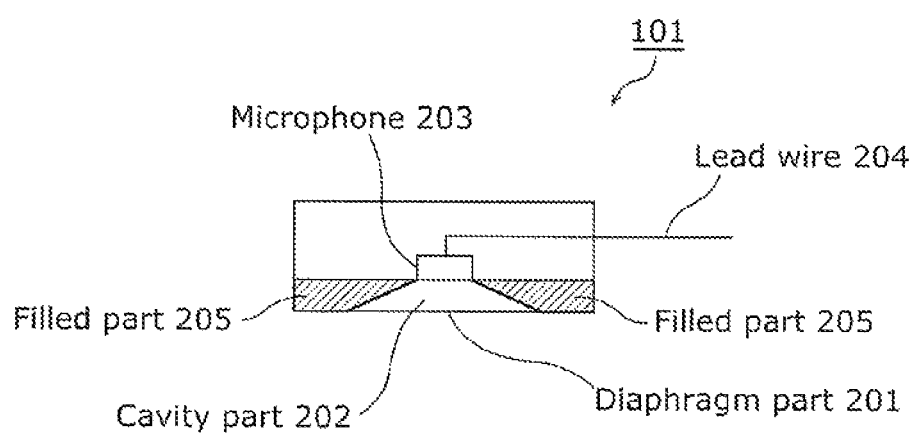
FIG. 2 is a configuration diagram of a physiological sound measurement unit.

FIG. 2 is a configuration diagram of the physiological sound measurement unit 101.

As shown in FIG. 2, the physiological sound measurement unit 101 includes: a diaphragm part 201 which converts vibration of the physiological sound propagating through the living body into air vibration; a cavity part 202 where the physiological sound converted into the air vibration by the diaphragm part 201 propagates; a microphone 203 which converts the physiological sound propagated through the cavity part 202 into an electric signal; and a lead wire 204 used for transmitting the physiological sound signal converted into the electric signal by the microphone 203. It is to be noted that the filled part 205 may be filled with a damping material, such as rubber or gel, so that vibration from outside ambient noise does not propagate through the cavity part 202. Furthermore, the physiological sound measurement unit 102 includes the same constituents as those of the physiological sound measurement unit 101.

Each of FIG. 3A, FIG. 3B, FIG. 3C, and FIG. 3D shows an example of the functional block of the signal analysis unit 106.

The signal analysis unit 106 includes: a power calculation unit 301; an illness-related high frequency power ratio calculation unit 303; a power ratio calculation unit 304; and an illness-related gain calculation unit 305. The power calculation unit 301 calculates power of plural frequency bands from each physiological sound signal digitized by the A/D processing unit 105. The illness-related high frequency power ratio calculation unit 303 calculates an illness-related high frequency power ratio from power of each of the frequency bands calculated by the power calculation unit 301. The power ratio calculation unit 304 calculates a power ratio using power of one or more frequency bands calculated by the power calculation unit 301, and calculates a high frequency gain and a low frequency gain. The illness-related gain calculation unit 305 calculates an illness-related gain from the high frequency gain and the low frequency gain. As shown in FIG. 3B and FIG. 3C, the signal analysis unit 106 may further include a reference power calculation units 302 and 312 each calculates a correction value of power of a different frequency band from power of a predetermined frequency band calculated by the power calculation unit 301. Furthermore, as shown in FIG. 3D, the signal analysis unit 106 may include a correction unit 306 which corrects the power ratio calculated by the illness-related high frequency power ratio calculation unit 303.

Figure 3A:
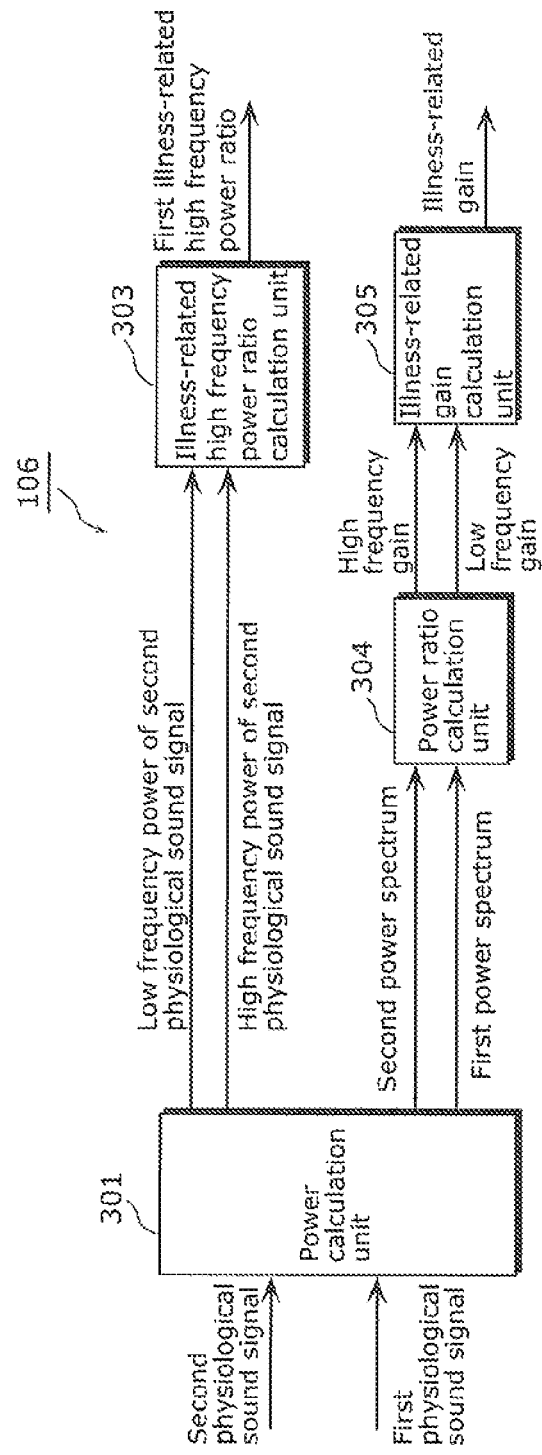
FIG. 3A shows an example of a functional block of a signal analysis unit.
Figure 3B:
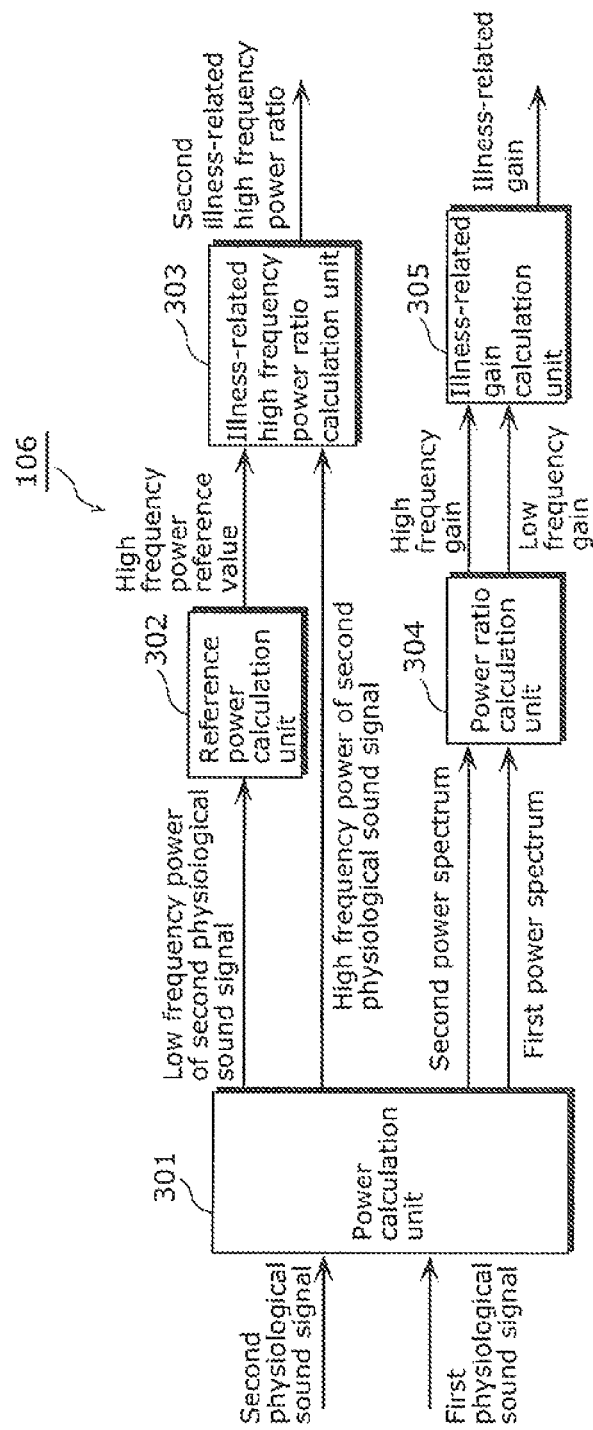
FIG. 3B shows another example of the functional block of the signal analysis unit.
Figure 3C:
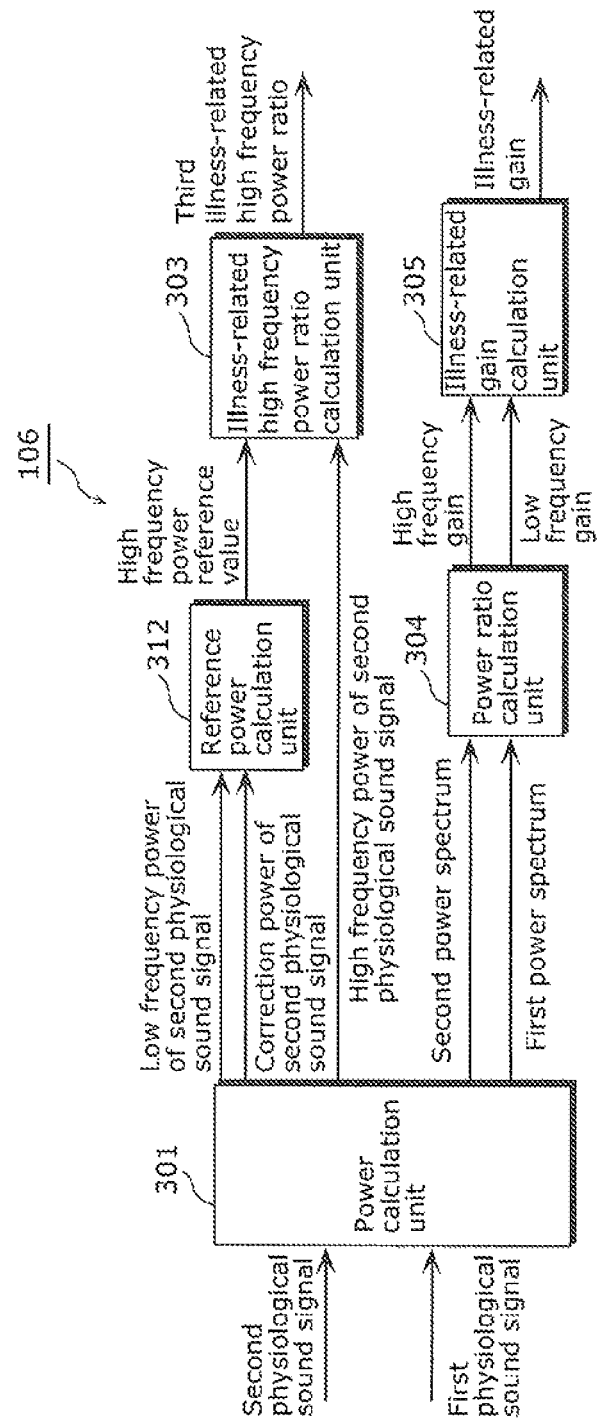
FIG. 3C shows another example of the functional block of the signal analysis unit.
Figure 3D:
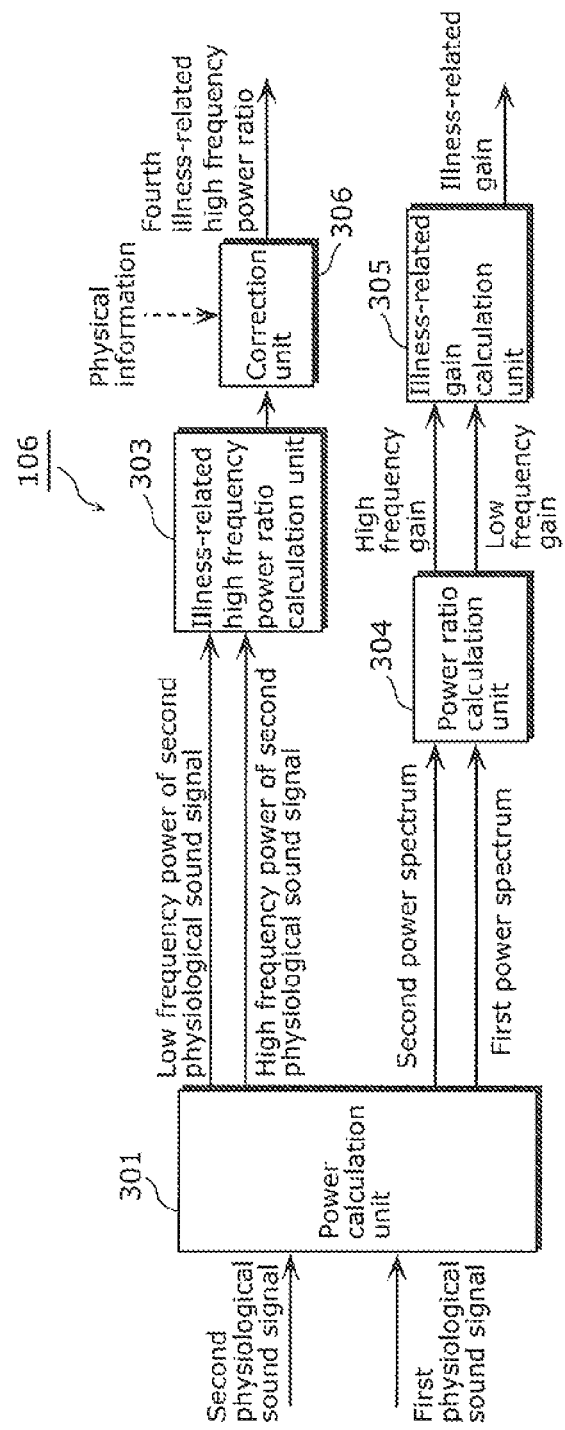
FIG. 3D shows the other example of the functional block of the signal analysis unit.

The illness-related high frequency power ratio is a value associated with a disease state of a trachea regardless of the respiratory flow velocity and the body size, and is calculated by a series of processing shown in each of FIG. 3A, FIG. 3B, FIG. 3C, and FIG. 3D. In order to clarify the difference due to the calculation method, the illness-related high frequency power ratio calculated by the processing shown in FIG. 3A is called a first illness-related high frequency power ratio. In the same manner, the illness-related high frequency power ratio calculated by the processing shown in FIG. 3B, FIG. 3C, and FIG. 3D are called a second illness-related high frequency power ratio, a third illness-related high frequency power ratio, and a fourth illness-related high frequency power ratio, respectively. It is to be noted that the illness-related high frequency power ratio is an example of the sound source characteristic index of the physiological sound.

It is to be noted that the illness-related gain is a value associated with a level of the disease state of the lung, regardless of the respiratory flow velocity and the body size. It is to be noted that the illness-related gain is an example of the transfer characteristic index of the physiological sound of the living body.

The following describes an operation performed by the physiological sound examination device 100 in order to obtain the illness-related high frequency power ratio and the illness-related gain, after the physiological sound signal is inputted.

First, a method of calculating the illness-related high frequency power ratio is described. It is to be noted that when the lung sound is measured as a second physiological sound, it is sufficient to place the physiological sound measurement unit 102 at a position closed to a central respiratory tract, which means a position close to the central respiratory tract on the chest wall, or the neck. A position closed to a sternal notch is particularly desirable. By placing the physiological sound measurement unit 102 close to a sternal notch, a sound source of breathing generated in a relatively thick respiratory tract can be measured at a high S/N (signal-noise) ratio because the distance between the central respiratory tract and the physiological sound measurement unit 102 can be shortened and attenuation of the lung sound caused by muscle or fat can be reduced.

Each of FIG. 4A, FIG. 4B, FIG. 4C, and FIG. 4D is a flowchart of a processing for calculating the illness-related high frequency power ratio, using the second physiological sound measured by the physiological sound measurement unit 102, in the signal analysis unit 106. The flowchart shown in FIG. 4A corresponds to a flow of processing in the functional block shown in FIG. 3B. In the same manner, FIG. 4B, FIG. 4C, and FIG. 4D correspond to FIG. 3C, FIG. 3A, and FIG. 3D, respectively.

First, the steps S400 and S401, which are processing common to all of the flowcharts shown in FIG. 4A, FIG. 4B, FIG. 4C, and FIG. 4D, are described.

Upon receiving the physiological sound signal digitized by the A/D processing unit 105, the power calculation unit 301 calculates the high frequency power that is power (sound pressure level) included in a high frequency (step S400). Here, the high frequency represents a frequency band in which the power of the lung sound can be significantly measured against the measured noise. The high frequency power is calculated by, for example, calculating power in the high frequency in a frame every 21 milliseconds, with one frame corresponding to 85 milliseconds, and calculating an average value of the high frequency power in each frame during analysis time period of the measured lung sound. It is to be noted that the high frequency power is an example of the first power.

Figure 5:
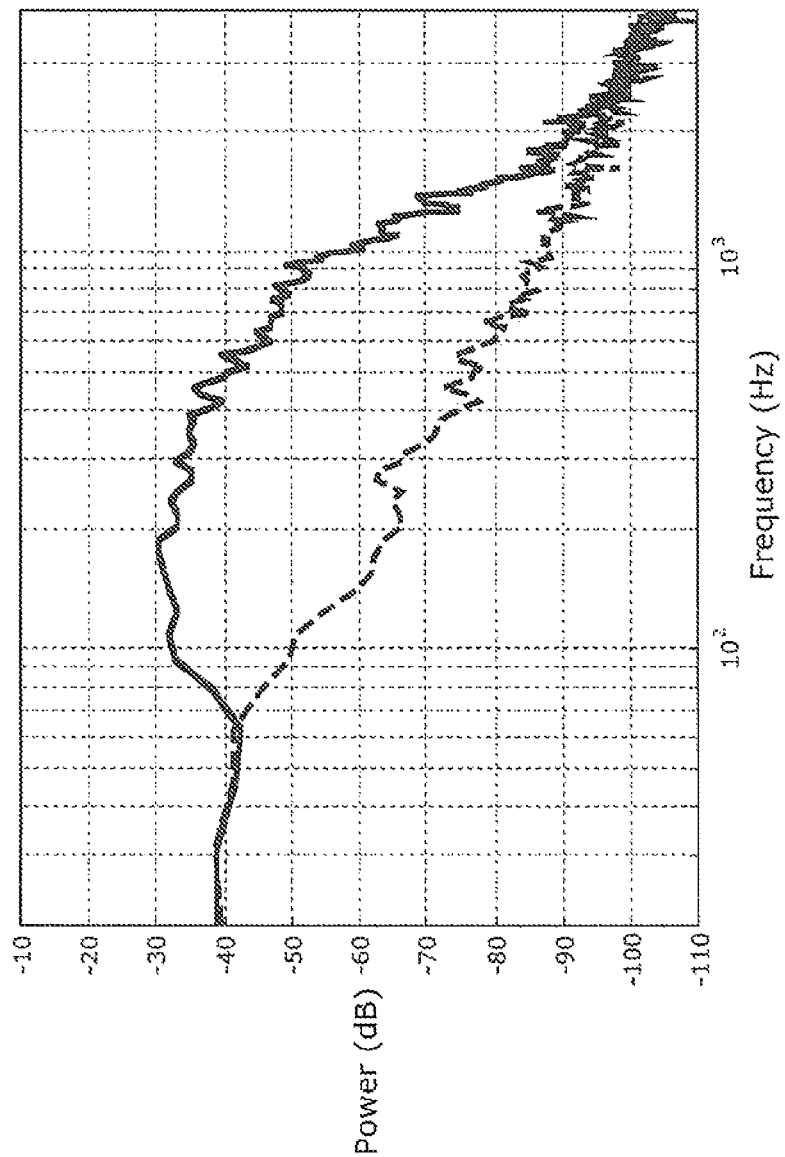
FIG. 5 shows an example of frequency response of power of a lung sound measured at a neck.

FIG. 5 shows an example of frequency response of power of a lung sound measured at a neck. The solid line indicates the frequency response of power of a lung sound measured during breathing. The broken line indicates the frequency response of power of a lung sound measured during non-breathing period. The measured lung sound includes noise and the frequency response measured during non-breathing period represents a noise level. A frequency band smaller than or equal to 4 kHz, in which the power of the lung sound and the noise level are equal, is appropriate for lung sound analysis. In particular, a frequency band smaller than or equal to 3 kHz, in which a lung sound spectral component of the lung sound with the S/N ratio (corresponding to the difference between the solid line and the broken line in FIG. 5) of greater than or equal to 5 dB is included, is appropriate. The S/N ratio is the power ratio of the lung sound to the noise level. Accordingly, as the high frequency, the frequency smaller than or equal to 3 kHz is appropriate, and particularly, a part or all of the frequency bands greater than or equal to 500 Hz and smaller than or equal to 1.5 kHz is desirable. It is to be noted that the high frequency power has a characteristic that variation in a respiratory tract caused by an illness is more likely to be reflected in the high frequency power, although the scope of the high frequency may vary in some degree for each illness or difference among individuals.

Next, the power calculation unit 301 calculates low frequency power that is the power included in the low frequency from the physiological sound signal digitized by the A/D processing unit 105 (step S401). For example, in the same manner as in the step S400, the power calculation unit 301 calculates the power included in the low frequency for each frame, and calculates the average value of the power in each frame in the analysis time period. As the low frequency, the frequency smaller than or equal to 3 kHz, in which the spectral component of the lung sound measured at the neck is included, and including a frequency band lower than the high frequency is sufficient. In particular, it is desirable for the frequency band to be greater than or equal to 100 Hz and smaller than or equal to 2 kHz. This is because this frequency band has a characteristic that the degree of the respiratory flow velocity during breathing is reflected in this frequency band. It is to be noted that the low frequency power is an example of the second power.

It is to be noted that the steps S400 and S401 are not limited to be processed in the above order and may be processed in the inverse order or in parallel.

Next, when the signal analysis unit 106 includes a reference power calculation unit 302 as shown, in FIG. 3B, the reference power calculation unit 302 calculates a high frequency power reference value for correcting the high frequency power from the measured low frequency power (step S402), using the low frequency power calculated by the power calculation unit 301 and a high frequency power correction formula that is set in advance in the recording unit 107.

The high frequency power correction formula can be expressed by Equation 1, for example.

$$DNPowNml=-0.006*DBPow^2+1.090*DBPow-4.19 \quad \text{(Equation 1)}$$

In Equation 1, DNPowNml represents the high frequency power reference value and DBPow represents a value of the low frequency power. Equation 1 is, for example, an equation that is derived as a regression curve of the low frequency power and the high frequency power of the lung sound measured at the neck of a subject with a normal lung, and an equation for predicting the high frequency power from the low frequency power. In this case, the high frequency power reference value is the high frequency power predicted from the low frequency power.

Figure 6:
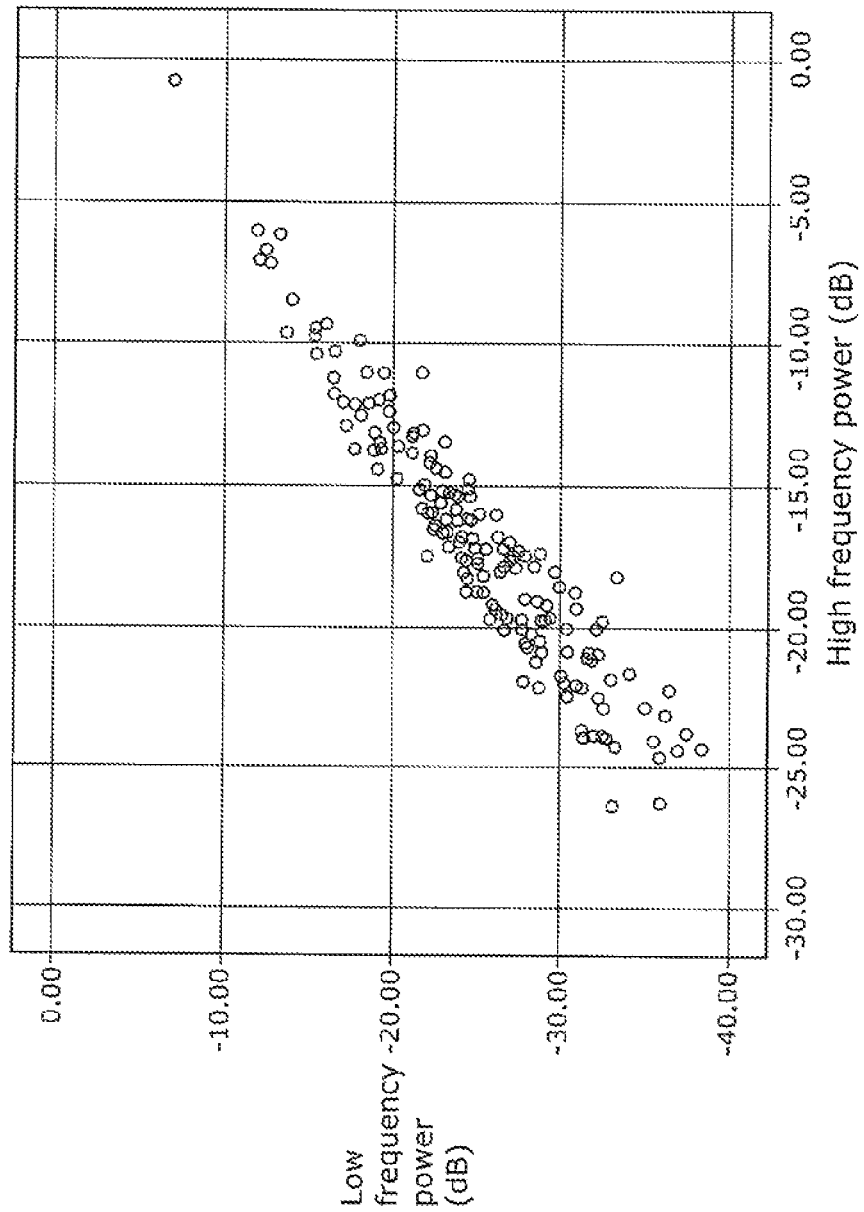
FIG. 6 is a scatter diagram showing an example of a relationship between a low frequency power and a high frequency power, of the measured lung sound.

Equation 1 is derived from the relationship between the low frequency power and the high frequency power of the lung sound measured at the neck. FIG. 6 shows an example of a scatter diagram illustrating the relationship between the low frequency power and the high frequency power of the lung sound measured at the neck. In the scatter diagram in FIG. 6, a regression curve having an order greater than or equal to first order can be used. Particularly, a regression curve having the highest correlation coefficient is the most appropriate. It is to be noted that in the measurement data shown in FIG. 6, the order of the regression curve having the highest correlation coefficient was the second order. It is to be noted that a different high frequency power correction formula may be used for each sensor to be used because the result is influenced by the characteristic of the sensor used to measure the lung sound.

Furthermore, it is sufficient that the high frequency power reference value is a value that can decrease the influence of the respiratory flow velocity, and may be obtained from an equation other than the regression curve or a regression line of the low frequency power and the high frequency power. For example, the equation may be an equation for calculating a value of the respiratory flow velocity from the low frequency power.

Figure 4A:
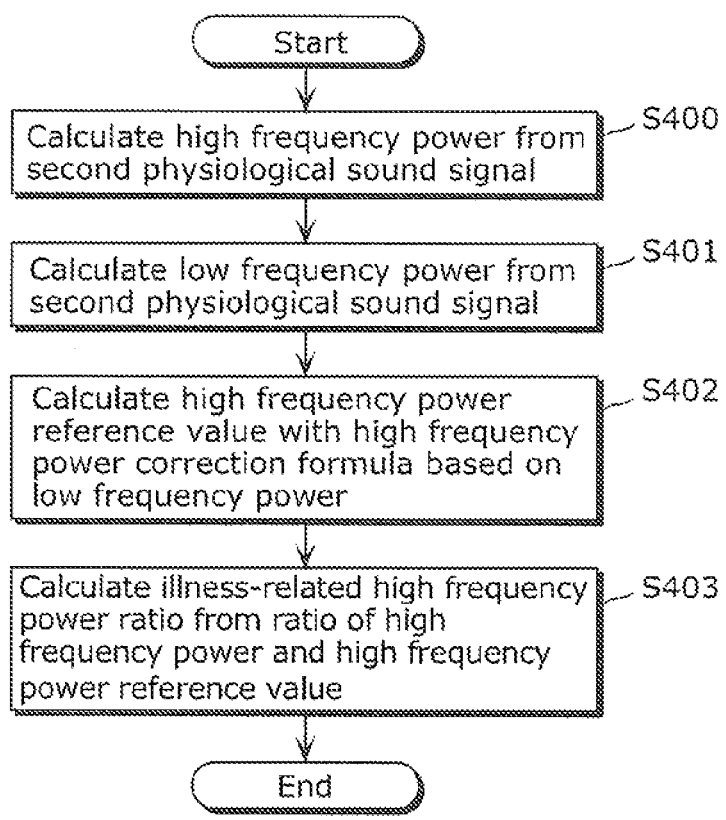
FIG. 4A is a flowchart showing an example of calculation of an illness-related high frequency power ratio.
Figure 4B:
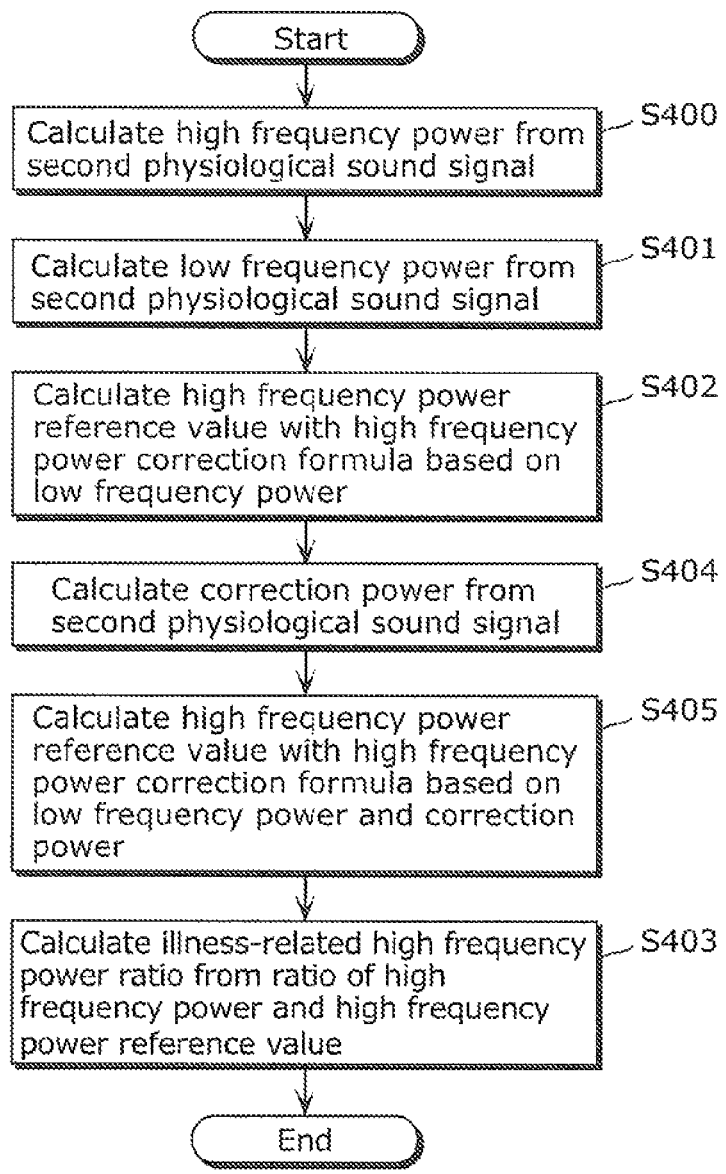
FIG. 4B is a flowchart showing another example of the calculation of the illness-related high frequency power ratio.

Next, when the signal analysis unit 106 includes the reference power calculation unit 312 as shown in FIG. 3C, the reference power calculation unit 312 calculates the high frequency power reference value, using the low frequency power calculated by the power calculation unit 301 and correction power. The flowchart of signal processing in this case is as shown in FIG. 4B.

The power calculation unit 301 calculates correction power that is included in a correction band of the physiological sound from the physiological sound signal digitized by the A/D processing unit 105 (step S404). For example, in the same manner as in the step S400, the power calculation unit 301 calculates the power included in the correction band for each frame, and calculates the average value of the power in each frame in the analysis time period. Because the spectral component of the lung sound measured at the neck is included in the frequency band smaller than or equal to 3 kHz, as the correction band, the band that is smaller than or equal to 3 kHz is sufficient. In particular, it is desirable for the frequency band to be greater than or equal to 100 Hz and smaller than or equal to 2 kHz. This is because this frequency band has a characteristic that the level of the respiratory flow velocity during breathing is reflected in this frequency band.

It is to be noted that the steps S400 and S401 are not limited to be processed in the above order and may be processed in the inverse order or in parallel.

Next, the reference power calculation unit 312 calculates the high frequency power reference value for correcting the high frequency power (step S405), using the low frequency power calculated by the power calculation unit 301, the correction power, and the high frequency power correction formula that is set in advance in the recording unit 107.

The high frequency power correction formula can be expressed by Equation 2, for example.

$$DNPowNml=DBPow+Coef\_C*CorPow \quad \text{(Equation 2)}$$

Here, DNPowNml and DBPow represent the same variables as in Equation 1, and CorPow represents the correction power. Coef_C represents a coefficient to be multiplied to CorPow. The first term on the right-hand side in Equation 2 represents a term of DBPow that is selected as a band that drastically decreases the influence of the respiratory flow velocity, and the second term on the right-hand side is a term for decreasing the influence of a factor other than the respiratory flow velocity.

Figure 24:
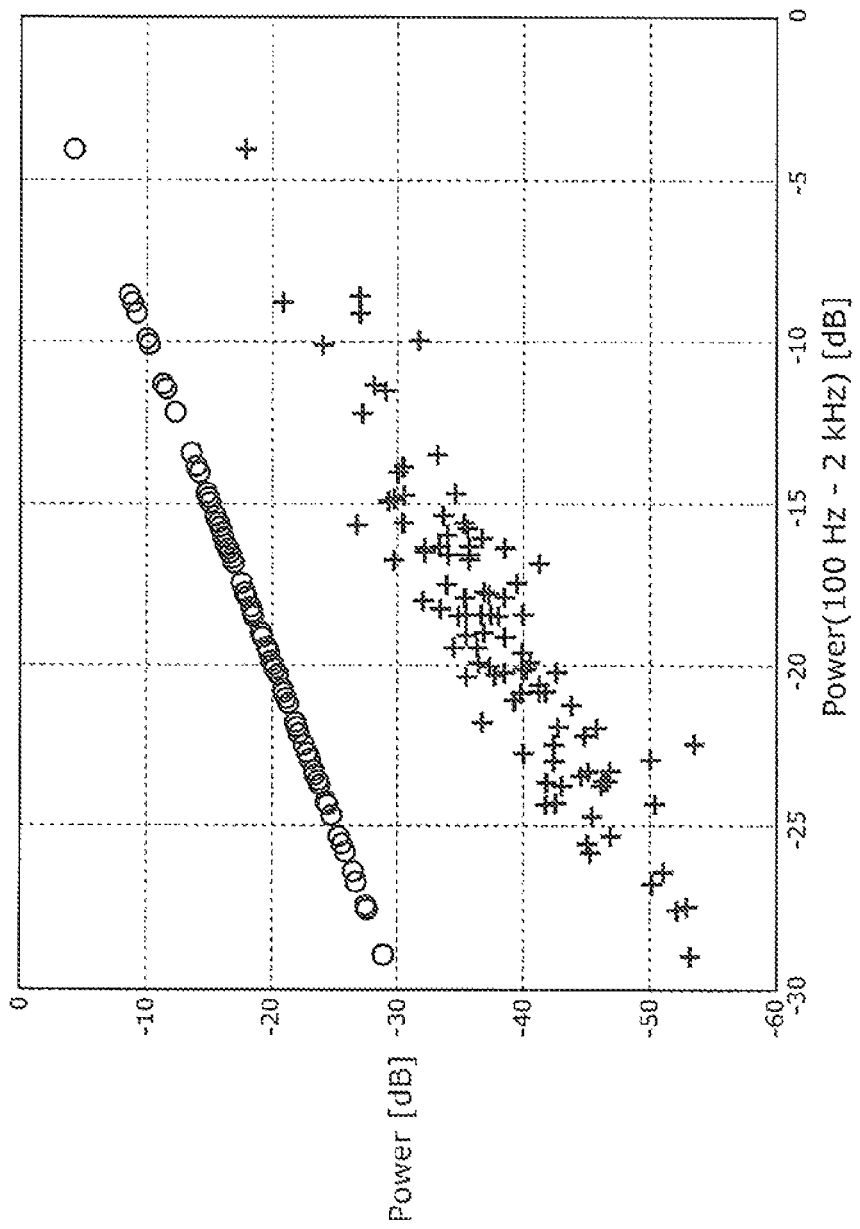
FIG. 24 is a scatter diagram showing an example of (i) a relationship between the power in all of the bands and the high frequency power and (ii) a relationship between the power in all of the bands and the low frequency power, of the measured lung sound.

FIG. 24 is a scatter diagram showing an example of (i) a relationship between the power in all of the bands and the high frequency power and (ii) a relationship between the power in all of the bands and the low frequency power, of the measured lung sound. In the scatter diagram in FIG. 24, the horizontal axis is for the power in all of the bands of the physiological sound, and the vertical axis is for the high frequency power and the low frequency power. In FIG. 24, the all-band power is greater than or equal to 100 Hz and smaller than or equal to 2 kHz, the high frequency power is greater than or equal to 800 Hz and smaller than or equal to 1.3 kHz, and the low frequency power is greater than or equal to 100 Hz and smaller than or equal to 800 kHz. Furthermore, the circle in the drawing indicates a plot of the low frequency power and the plus indicates a plot of the high frequency power. A regression line defined by the low frequency power and the all-band power is expressed by Equation 3, and a regression line defined by the high frequency power and the all-band power is expressed by Equation 4.

$$DBPow=Coef\_B*Allpow+Const\_B \quad \text{(Equation 3)}$$

$$DNPow=Coef\_N*Allpow+Const\_N \quad \text{(Equation 4)}$$

DBPow is the low frequency power, DNPow is the high frequency, power, and AllPow is the all-band power. Furthermore, Coef_B and Coef_N are coefficients representing gradients, and in this experiment, Coef_B was 0.99 and Coef_N was 1.41. Const_B and Const_N are coefficients representing intercepts.

As shown in FIG. 24, the plots in the low frequency power vary in a narrow range and approximately linearly in proportion to the all-band power. Meanwhile, the plots in the high frequency power vary in a wide range and the gradient is different from the gradient in the low frequency power, though it varies in proportion to the all-band power. The difference between the gradients may be caused by the influence of the difference among individuals and the difference in the body sizes, which are the factors other than the respiratory flow velocity, and it is desirable to reduce such influences.

Therefore, as in the second term on the right-hand side of Equation 2, a term resulting from multiplying Coef_C to CorPow, with the difference value between Coef_B and Coef_N corresponding to Coef_C, is added. The frequency band for CorPow may be any frequency band out of the frequency bands for the all-band power or the low frequency power, and it is sufficient that the frequency band for CorPow is different from the high frequency. In particular, a frequency band that does not overlap with the high frequency is desirable. Furthermore, the coefficient of the second term on the right-hand side of Equation 2 is the coefficient obtained through the experiment, and other coefficients may be used. It goes without saying that the term other than the linear function, such as an exponentiation term, may be used. It is to be noted that when the frequency band for CorPow is the same frequency band as that of the low frequency power, the signal analysis unit 106 may include the reference power calculation unit 302 as shown in FIG. 3B.

For each of the correction formulas Equation 1 and Equation 2, a different correction formula may be selected depending on physical information such as an illness, a race, a target age, a height, an age, a weight, and a gender, or a purpose of use. Furthermore, at least one parameter as the above may be introduced to the correction formula as at least one variable. Moreover, the frequency band for the low frequency power or the correction power may be optionally selected at the selection of the correction formula. The frequency band may be selected based on the form of each of the power spectrum of the first physiological sound and the second physiological sound.

Next, the illness-related high frequency power ratio calculation unit 303 calculates a third illness-related high frequency power ratio, using the high frequency power calculated by the power calculation unit 301 and the high frequency power reference value calculated by the reference power calculation unit 312. The illness-related high frequency power ratio is obtained as a ratio of the high frequency power to the high frequency power reference value (step S403).

Figure 4C:
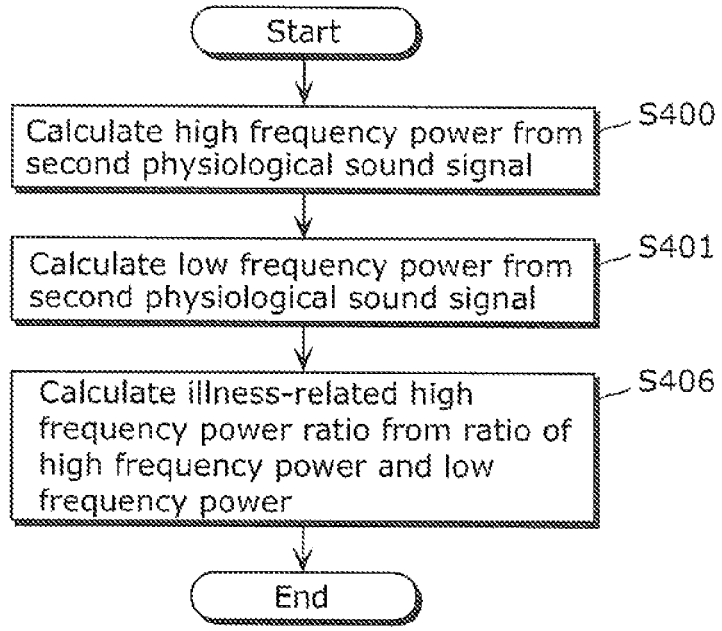
FIG. 4C is a flowchart showing another example of the calculation of the illness-related high frequency power ratio.

Furthermore, the low frequency power may be used as the high frequency power reference value if the band to which the influence of the respiratory flow velocity is reflected is selected as the frequency band for the low frequency power. In this case, the reference power calculation units 302 and 312 are not required, the signal analysis unit 106 is configured as shown in FIG. 3A and FIG. 4C for example, and the illness-related high frequency power ratio calculation unit 303 calculates the ratio of the high frequency power to the low frequency power as the first illness-related high frequency power ratio (step S406).

In this case, it is sufficient that the frequency band for the low frequency power is smaller than or equal to 3 kHz, in which the spectral component of the lung sound measured at the neck is included, as shown in FIG. 5. In particular, it is desirable for the frequency band to be greater than or equal to 100 Hz and smaller than or equal to 800 Hz. It is because the power of this frequency band has characteristics that it varies approximately linearly in proportion to the respiratory flow velocity as shown in FIG. 24 and that it can decrease the overlap with the frequency band for the high frequency power to which the influence of the illness is reflected.

Figure 4D:
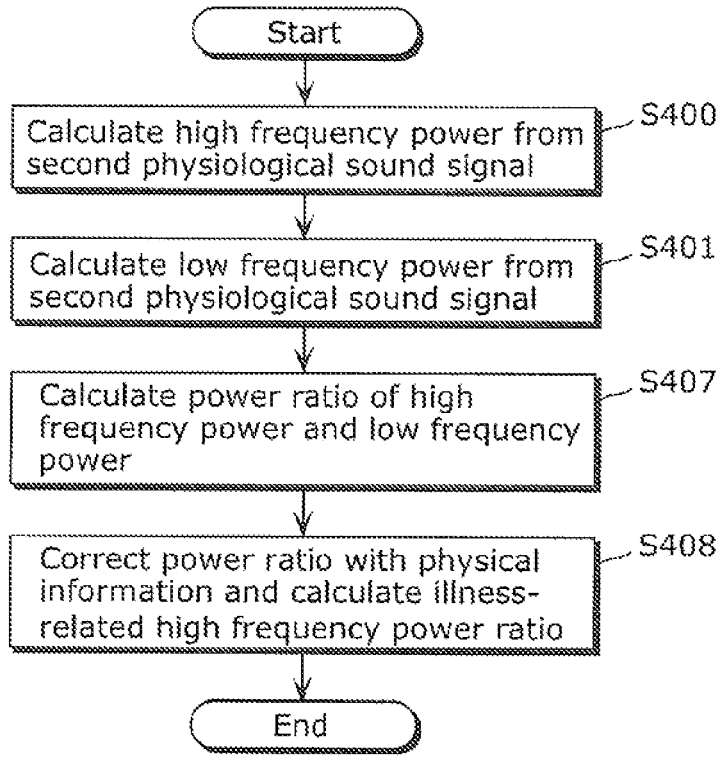
FIG. 4D is a flowchart showing the other example of the calculation of the illness-related high frequency power ratio.

In addition, as shown in FIG. 4D, the power ratio calculated from the low frequency power and the high frequency power may be corrected using the physical information, to calculate a fourth illness-related high frequency power ratio (step S407). In this case, the signal analysis unit 106 is configured as shown in FIG. 3D, and the correction unit 306 corrects the power ratio calculated by the illness-related high frequency power ratio calculation unit 303. It is to be noted that an example of the physical information includes the height, the age, the weight, the body surface area, and the body mass index. As a method of correction, the power ratio may be divided by the value of the physical information. Another method includes calculating a power ratio prediction formula by regression analysis or the like using (i) the power ratio calculated from the lung sound of a normal person and (ii) at least one variable out of the physical information as an independent variable. When the correction unit 306 performs correction, the correction unit 306 may perform the correction by calculating a power ratio reference value obtained from the physical information and the power ratio prediction formula, and with using the ratio of or the difference between the power ratio reference value and the power ratio calculated by the illness-related high frequency power calculation unit 303.

Figure 25A:
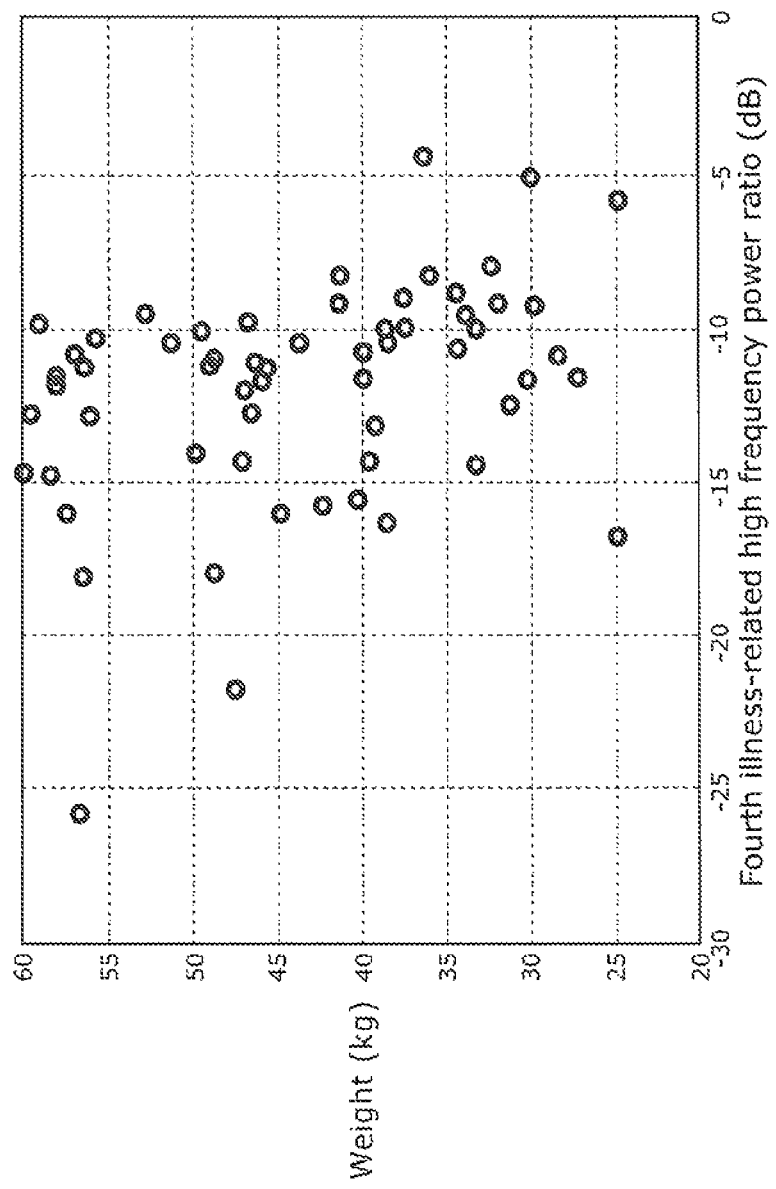
FIG. 25A is a scatter diagram showing an example of a relationship between the illness-related high frequency power ratio and weight.

FIG. 25A is a scatter diagram showing an example of a relationship between the weight and the illness-related high frequency power ratio calculated by the illness-related high frequency power ratio calculation unit 303. As shown in FIG. 25A, a significant negative correlation can be seen between the power ratio and weight (correlation coefficient=−0.456, significance probability<0.01).

FIG. 25B is a scatter diagram showing an example of a relationship between the height and the illness-related high frequency power ratio calculated by the illness-related high frequency power ratio calculation unit 303. As shown in FIG. 25B, a significant negative correlation can be seen between the power ratio and weight (correlation coefficient=−0.368, significance probability<0.01). There is a correlation between the power ratio and height and between the power ratio and weight, and therefore it is desirable to perform correction based on the physical information.

It is to be noted that the frequency band for the high frequency power may be different depending on the physical information such as an illness, a race, a target age, a height, an age, a weight, and a gender, or a purpose of use. Furthermore, the frequency band may be selected based on the form of each of the power spectrum of the first physiological sound and the second physiological sound.

The illness-related high frequency power ratio may be obtained as a ratio by taking one of the powers as a reference, in all of the cases shown in FIG. 4A, FIG. 4B, FIG. 4C, and FIG. 4D. However, the following takes the case shown in FIG. 4A as an example and assumes that the ratio is obtained by taking the high frequency power reference value as a reference.

Figure 10:
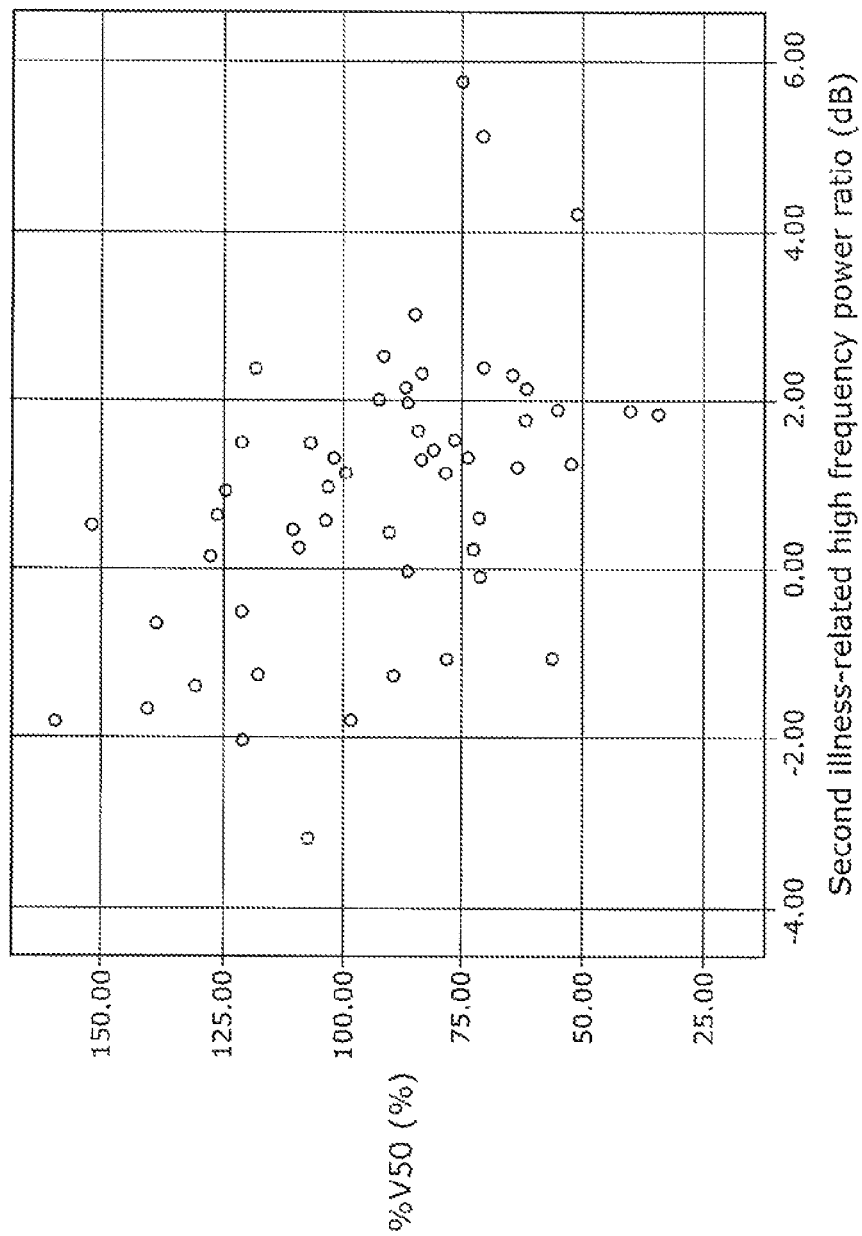
FIG. 10 is a scatter diagram showing an example of a relationship between the illness-related high frequency power ratio and %V50 of a spirometer, of an asthma patient.

FIG. 10 is a scatter diagram showing an example of a relationship between the illness-related high frequency power ratio and %V50 (prediction rate of air speed at an air amount level of 50% of lung capacity) that is an index of a spirometer, of an asthma patient. As shown in FIG. 10, a significant negative correlation can be seen between the illness-related high frequency power ratio and %V50 (correlation coefficient=−0.494, significance probability<0.001). It is said that %V50 represents an occluded state of a respiratory tract, and the respiratory tract is more occluded as the value of %V50 is smaller. As shown in FIG. 10, there is a significant correlation between the illness-related high frequency power ratio and %V50. Therefore, it can be said that the occluded state of a respiratory tract is reflected on the illness-related high frequency power ratio.

Figure 26A:
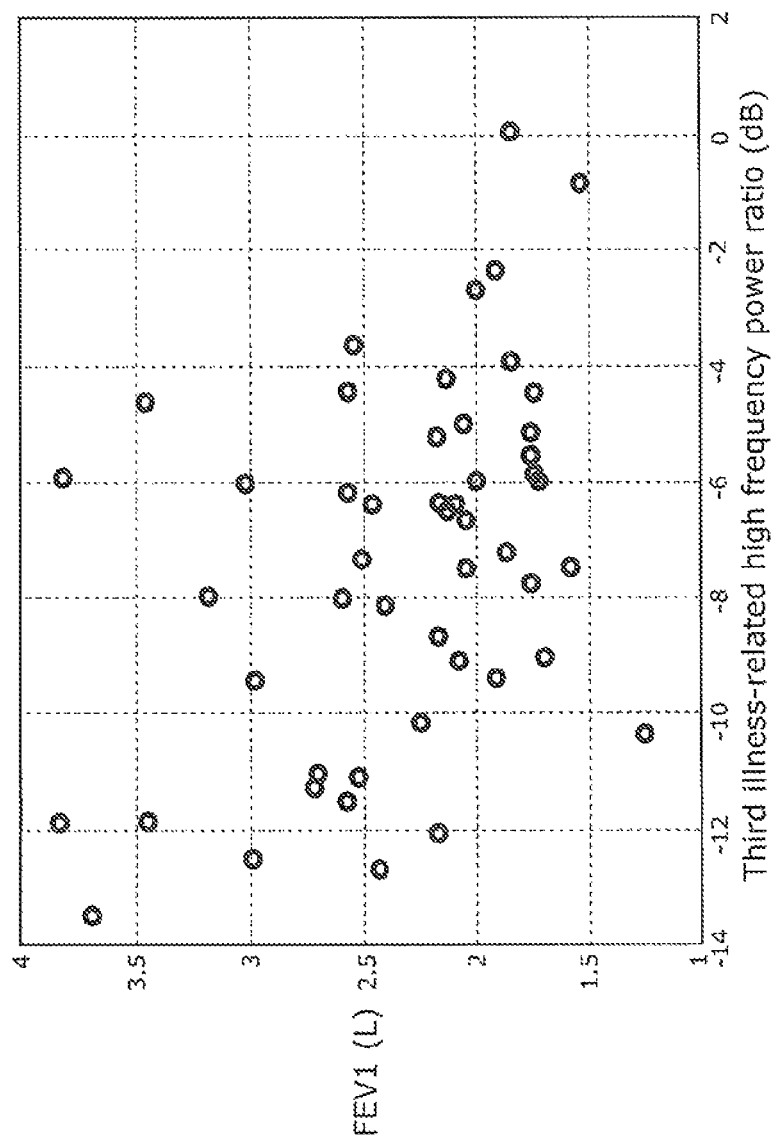
FIG. 26A is a scatter diagram showing an example of a relationship between the illness-related high frequency power ratio and FEV1.

FIG. 26A is a scatter diagram showing an example of a relationship between the illness-related high frequency power ratio obtained by the flowchart in FIG. 4B and forced expiratory volume in 1 second (FEV1) that is an index of the spirometer, of an asthma patient. In FIG. 26A, a significant negative correlation can be seen between the illness-related high frequency power ratio and FEV1 (correlation coefficient=−0.415, significance probability<0.01).

Figure 26B:
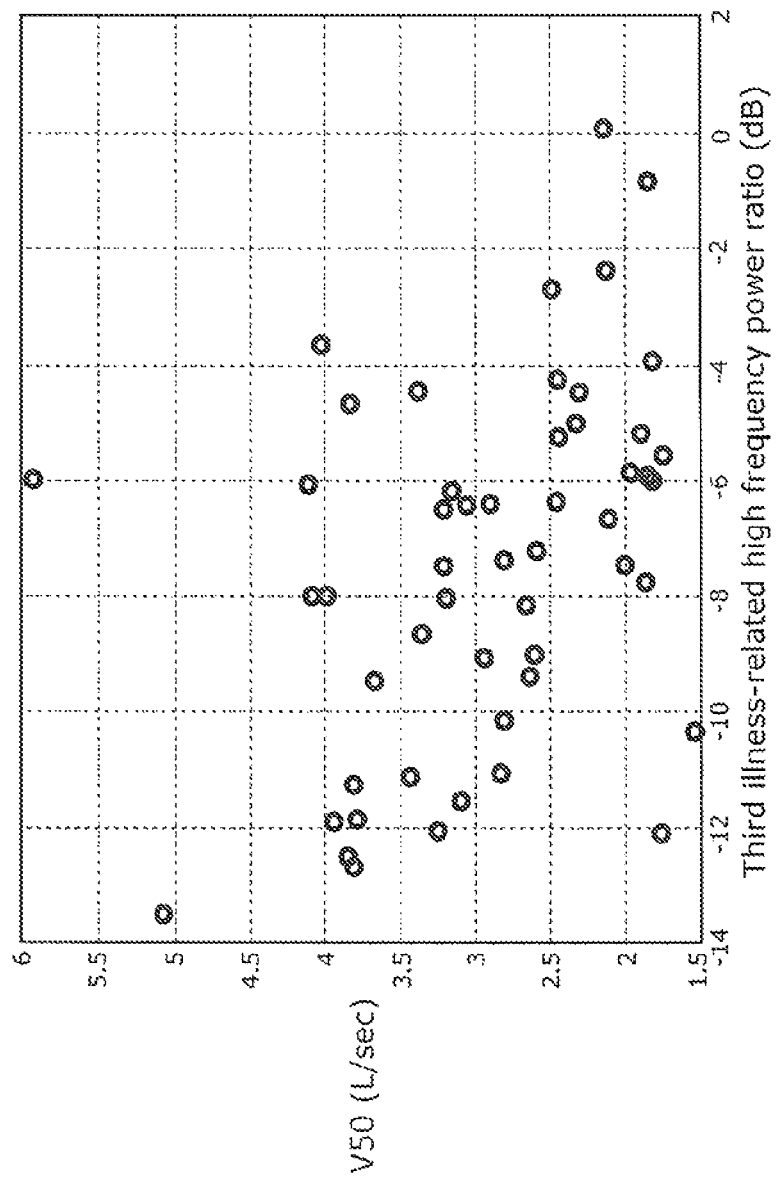
FIG. 26B is a scatter diagram showing an example of a relationship between the illness-related high frequency power ratio and V50.

FIG. 26B is a scatter diagram showing an example of a relationship between the illness-related high frequency power ratio obtained by the flowchart in FIG. 4B and V50 (actual measured value of air speed at the air amount level of 50% of lung capacity) that is an index of the spirometer, of an asthma patient. In FIG. 26B, a significant negative correlation can be seen between the illness-related high frequency power ratio and V50 (correlation coefficient=−0.376, significance probability<0.01). It is said that FEV1 and V50 represent the occluded state of the respiratory tract, and the respiratory tract is more occluded as the values of FEV1 and V50 are smaller.

Figure 27A:
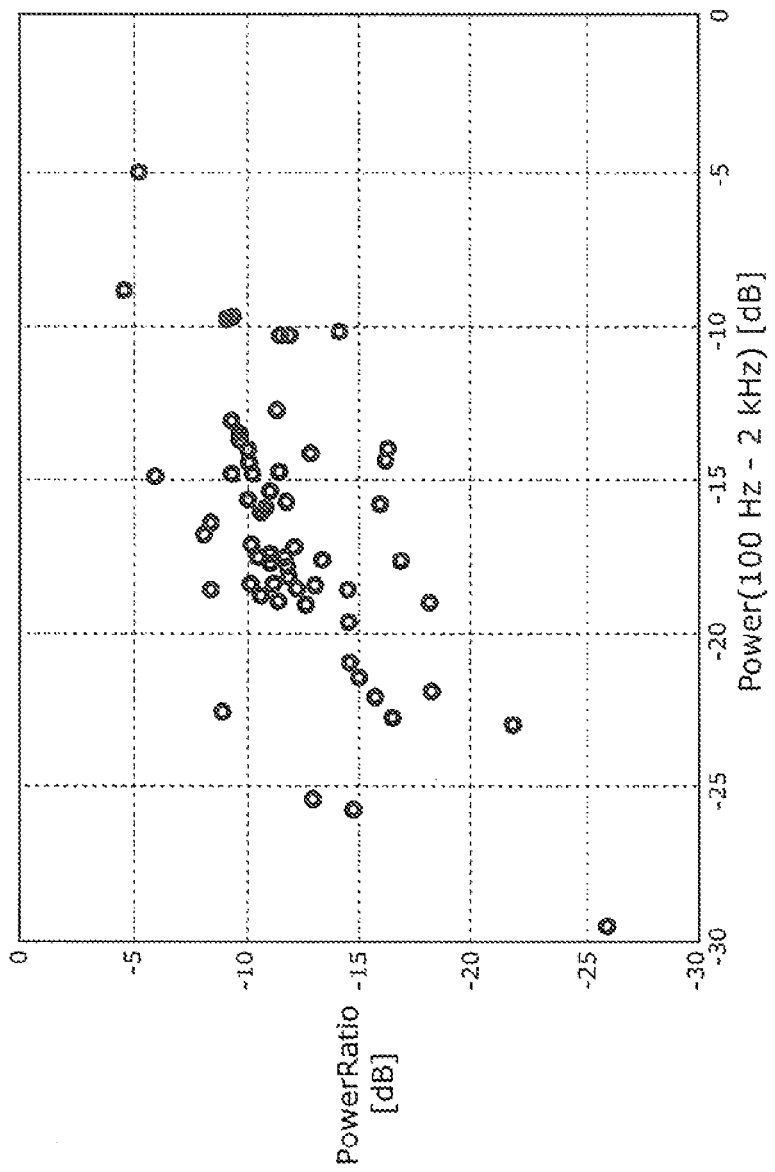
FIG. 27A is a scatter diagram showing an example of a relationship between the all-band power and the illness-related high frequency power ratio, of the physiological sound.

Each of FIG. 27A and FIG. 27B is a scatter diagram showing an example of a relationship between the all-band power and the illness-related high frequency power ratio of the physiological sound obtained by the configuration shown in FIG. 3A and FIG. 3C, respectively. A band used for the all-band power is greater than or equal to 100 Hz and smaller than or equal to 2 kHz. According to FIG. 27A, the illness-related high frequency power ratio calculated by the configuration shown in FIG. 3A is a value that depends on the all-band power. However, according to FIG. 27B, the illness-related high frequency power ratio calculated by the configuration shown in FIG. 3C is a value that is independent from the all-band power. With the configuration shown in FIG. 3C, a value independent from the all-band power, that is a value with the reduced influence of the respiratory flow velocity, the difference among individuals, and the difference in the body sizes, is likely to be calculated, though it is required to set a coefficient of Equation 2 in advance. Meanwhile, with the configuration shown in FIG. 3A, the setting of coefficient is not required and there is a few problems in using the illness-related high frequency power ratio in time series comparison for one person where the influence of the difference among individuals and the difference in the body sizes is relatively small.

As described above, the physiological sound examination device 100 can quantify a state inside a respiratory tract caused by an illness using an illness-related high frequency power ratio.

For example, in the case of excess of secretion and roughening of respiratory tract surface, the high frequency power of noise due to disturbed flow, that is the breath sound source, increases and the value of the illness-related high frequency power ratio may increase. Meanwhile, the high frequency power of the noise due to disturbed flow may decrease and the value of the illness-related high frequency power ratio may be smaller, as the lung becomes closer to a normal state.

The physiological sound examination device 100 can decrease the influence of the respiratory flow velocity by using the illness-related high frequency power ratio, that is resulted from calculating the ratio of the high frequency power to the high frequency power reference value calculated using the high frequency power correction formula, instead of directly using the high frequency power that varies depending on the respiratory flow velocity.

As a result, there is no need to direct a subject to adjust the respiratory flow velocity. Furthermore, there is no need to measure a lung sound and respiratory flow velocity simultaneously by using a spirometer or the like and to perform some corrections using the respiratory flow velocity by signal processing. Accordingly, with the physiological sound examination device 100, the state of the respiratory tract can be easily evaluated only by measuring a lung sound.

It is to be noted that the power calculation unit 301 may calculate power in each of the frequency bands by calculating power of a desired frequency band, using frequency conversion such as Fourier conversion, using a bandpass filter, or by another method.

Although the reference power calculation unit 302 has calculated the high frequency power reference value using the low frequency power and the high frequency power correction formula, when breathing flow is measured using a spirometer or the like in an actual examination, the high frequency power reference value may be calculated using the respiratory flow velocity measured by using a breathing flow sensor. In this case, it is required to preliminarily record, in the recording unit 107, a correction formula for calculating the high frequency power reference value from the respiratory flow velocity. As a result, the influence of the respiratory flow velocity to the high frequency power can be reduced with a higher degree of accuracy.

Next, a method of calculating the illness-related gain is described. When the lung sound is measured as the physiological sound, it is sufficient to place the physiological sound measurement unit 101 on a chest wall or a back, and a position around the lung is desirable. In particular, on the second intercostal space on the right midclavicular line is desirable. It is because the propagation distance of the lung sound in the lung parenchyma can be as long as possible and the influence of elements other than the lung parenchyma, such as muscle or fat, to the lung sound propagation can be reduced. The variation in the state of the lung parenchyma caused by the illness can be caught with high sensitivity by the variation in the lung sound as the lung sound propagation distance in the lung parenchyma is longer. Furthermore, the second intercostal space on the right midclavicular line is far from the heart and therefore the heart sound is not mixed much, whereby the lung sound can be measured at a high S/N ratio.

Figure 7:
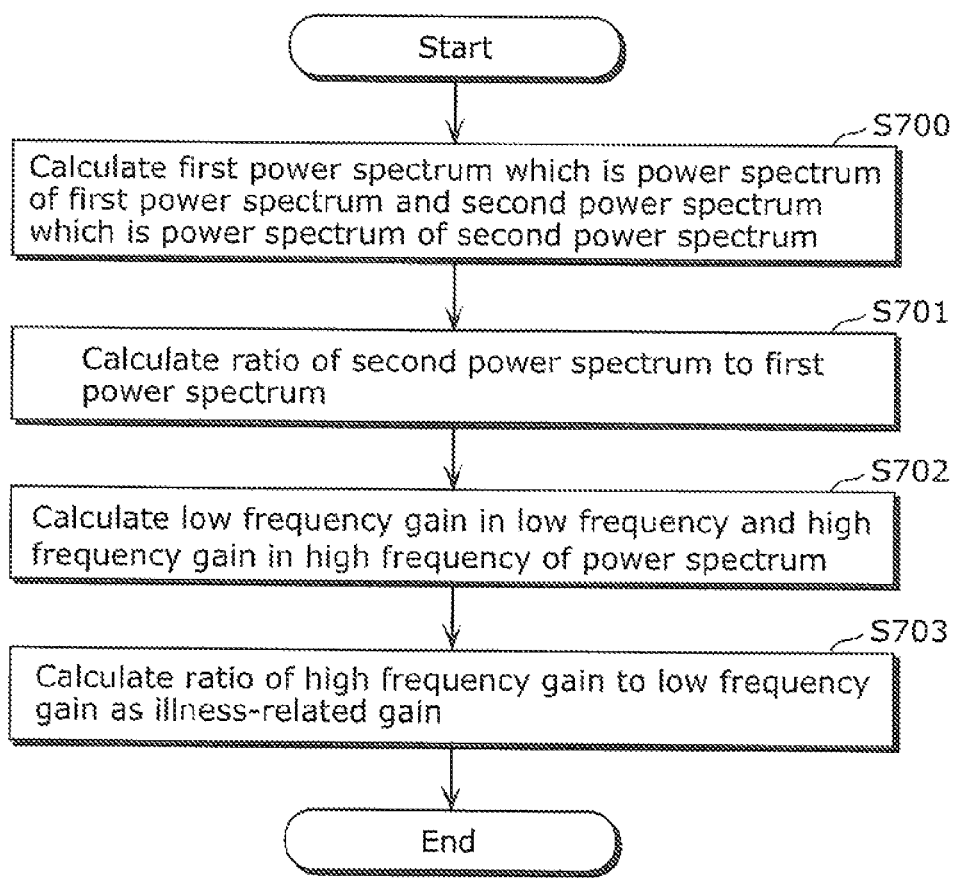
FIG. 7 is a flowchart showing an example of a method of calculating an illness-related gain.

FIG. 7 is a flowchart showing an example of a method of calculating an illness-related gain, performed by the signal analysis unit 106, using the first physiological sound and the second physiological sound measured by the physiological sound measurement unit 101 and the physiological sound measurement unit 102, respectively.

Upon receiving the first physiological sound signal and the second physiological sound signal digitized by the A/D processing unit 105, the power calculation unit 301 calculates a first power spectrum and a second power spectrum which are the power spectra in all of the frequency bands of each physiological sound signal (step S700). The first power spectrum and the second power spectrum are obtained by, for example, calculating a power spectrum in a frame every 21 milliseconds using frequency conversion, with one frame corresponding to 85 milliseconds, and calculating an average value of the power spectrum in each frame during analysis time period of the measured lung sound.

The power ratio calculation unit 304 calculates a ratio of the first power spectrum to the second power spectrum using the first power spectrum and the second power spectrum calculated by the power calculation unit 301 (step S701). It is to be noted that the power spectrum ratio may be obtained as a ratio by taking one of the first power spectrum and the second power spectrum as a reference. That is, the ratio of the second power spectrum to the first power spectrum may be used.

Next, a low frequency gain that is the power ratio in the low frequency and a high frequency gain that is the power ratio in the high frequency, of the calculated power spectrum ratio, are calculated (step S702).

Figure 8:
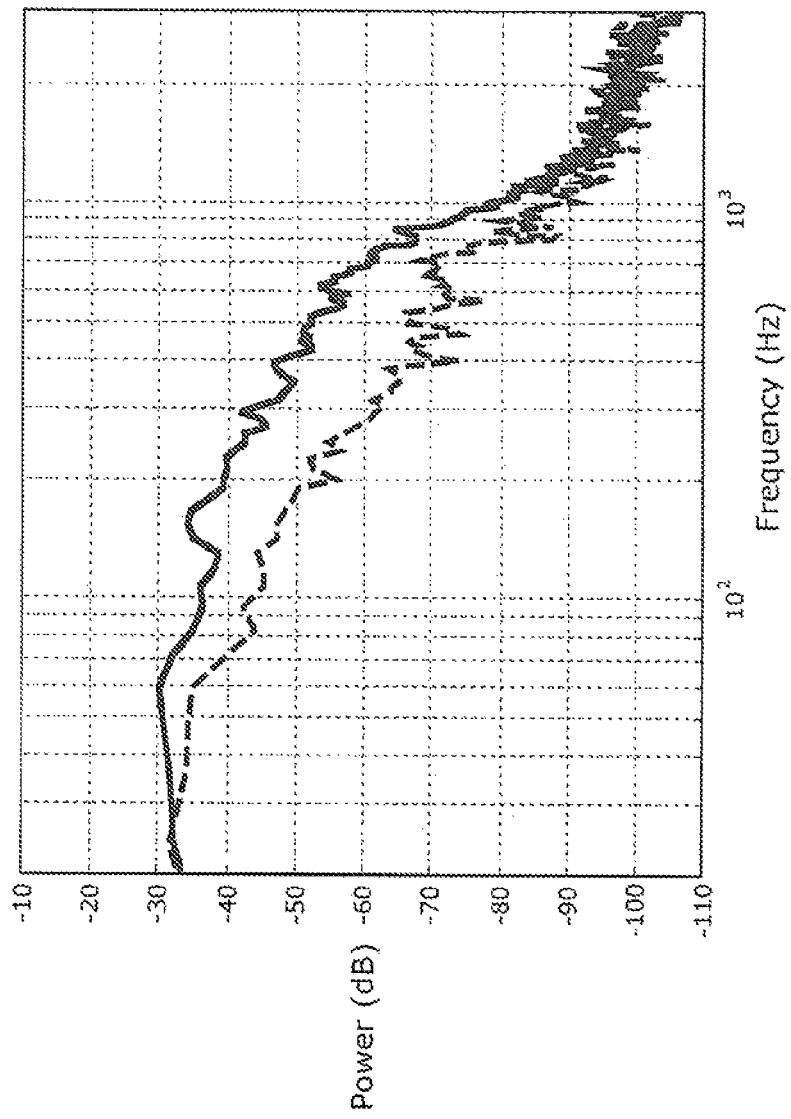
FIG. 8 shows an example of frequency response of power of a lung sound measured at a chest.

FIG. 8 shows an example of frequency response of power of the lung sound measured at the chest. The solid line represents the frequency response of the power of the lung sound measured during breathing, and the broken line represents the frequency response of the power measured during non-breathing period. The measured lung sound includes noise, and the frequency response measured during non-breathing period represents the noise level. A frequency band smaller than or equal to 3 kHz, in which the power of the lung sound and the noise level are equal, is appropriate for lung sound analysis. In particular, a frequency band smaller than or equal to 2 kHz, in which the lung sound spectral component of the lung sound with the S/N ratio (corresponding to the difference between the solid line and the broken line in FIG. 8) of greater than or equal to 5 dB is included, is appropriate. The S/N ratio is the power ratio of the lung sound to the noise level.

Figure 9:
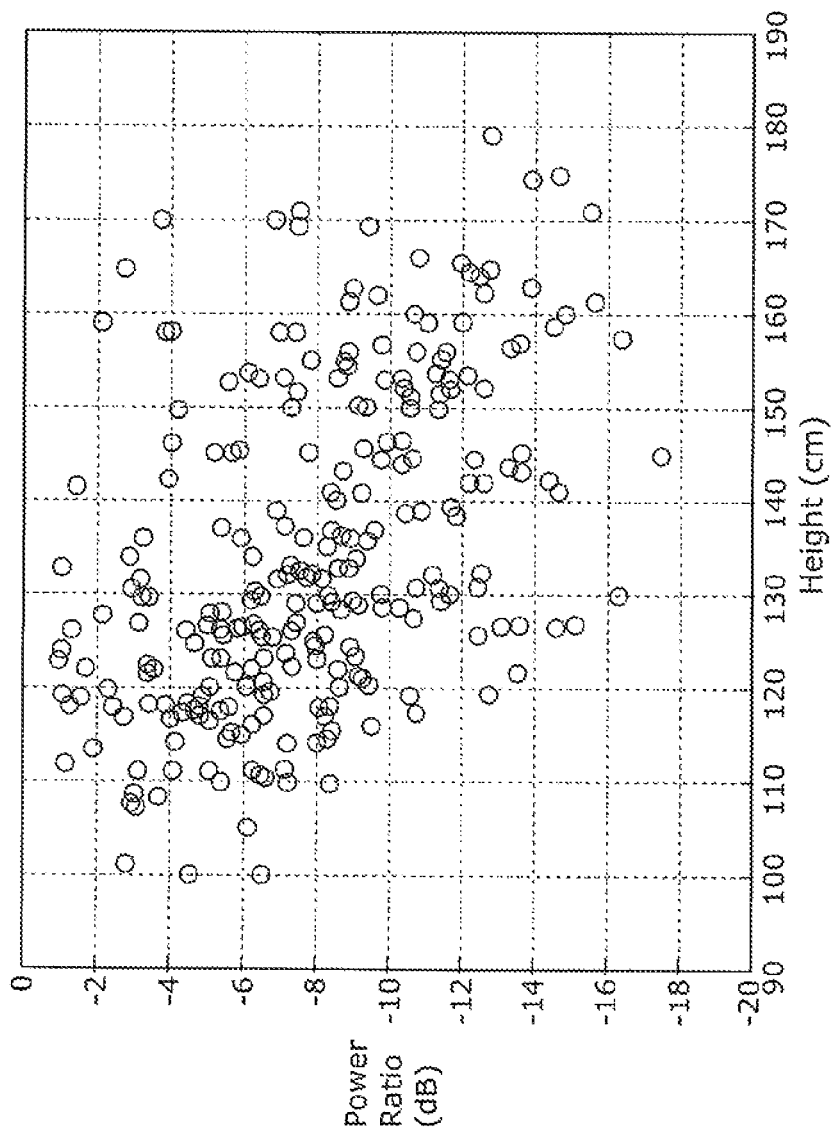
FIG. 9 is a scatter diagram showing an example of a relationship between a measured height and low frequency gain.

Accordingly, a frequency band smaller than or equal to 2 kHz is appropriate for the low frequency band, and particularly, it is desirable for the band to be greater than or equal to 100 Hz and smaller than or equal to 200 Hz. For example, it is appropriate to set, as the low frequency gain, the average value of the power ratio included in the band greater than or equal to 100 Hz and smaller than or equal to 200 Hz. It is because this frequency has a characteristic that the body size of the subject is reflected to this frequency band. FIG. 9 is a scatter diagram showing an example of a relationship between the measured height and low frequency gain. As shown in FIG. 9, a significant negative correlation can be seen between the height and the low frequency gain (correlation coefficient=−0.484, significance probability<0.001), and it can be understood that the body size of the subject is apparent from the low frequency gain.

Furthermore, it is sufficient that the high frequency is a frequency band which includes a frequency component greater than or equal to the frequency in the low frequency and is smaller than or equal to 2 kHz. In particular, it is desirable for the frequency band to be in a 400 Hz band including approximate 400 Hz. It is because this frequency band has a characteristic that the state of the lung parenchyma caused by the illness is reflected to this frequency band.

Next, the illness-related gain calculation unit 305 calculates, as the illness-related gain, a ratio of the high frequency gain to the low frequency gain, using the low frequency gain and the high frequency gain calculated by the power ratio calculation unit 304 (step S703). It is to be noted that the illness-related gain may be obtained as a ratio by taking one of the low frequency gain and the high frequency gain as a reference. That is, the ratio of the low frequency gain to the high frequency gain may be used.

Figure 11:
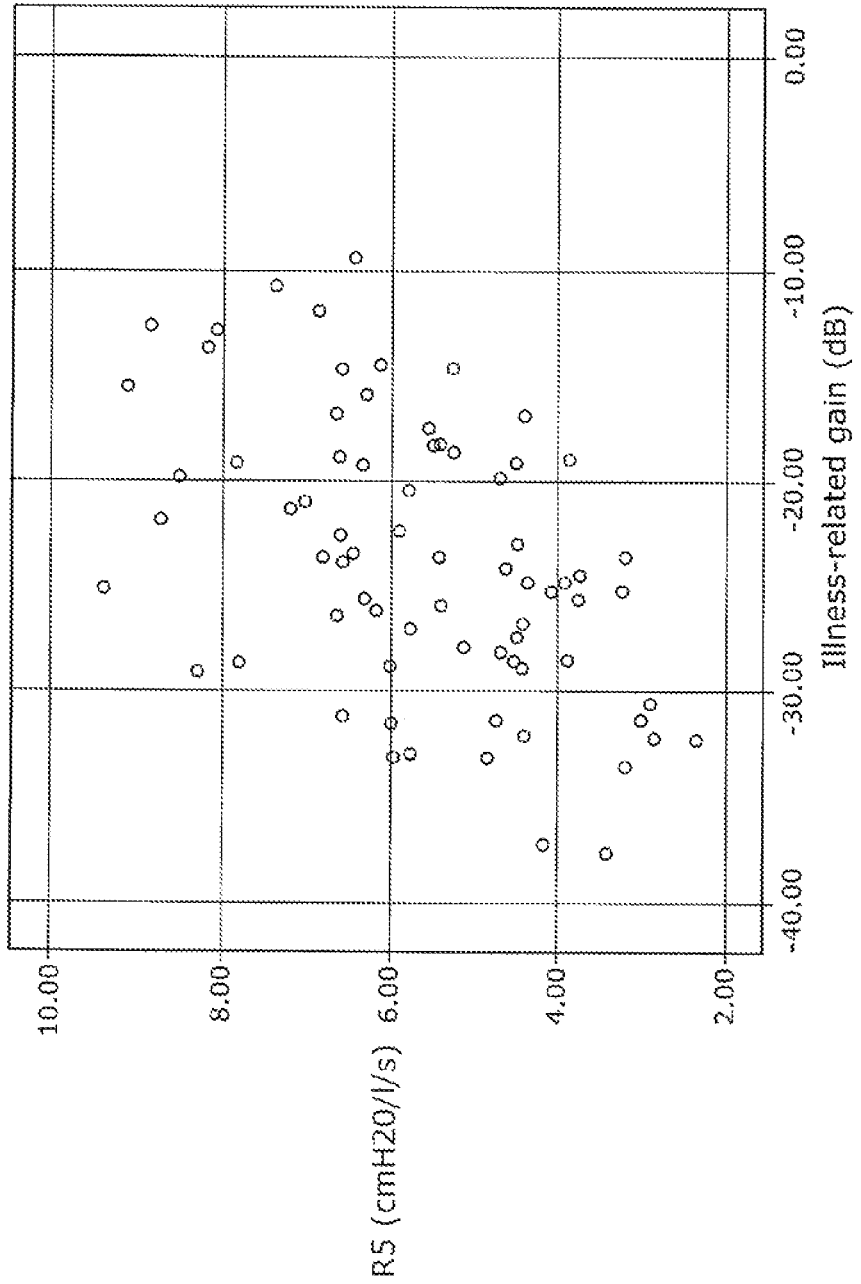
FIG. 11 is a scatter diagram showing an example of a relationship between the illness-related gain and R5 of IOS, of an asthma patient.

FIG. 11 is a scatter diagram showing an example of a relationship between the illness-related gain and R5 that is an index of Impulse Oscillometry System (IOS), of an asthma patient. It is to be noted that the index of IOS is a value that depends on an age, a height and a weight. However, a correction formula for the Japanese who are the subjects has not yet been established.

Therefore, in FIG. 11, in order for comparison with the actual measured value of IOS, a value of the high frequency gain, that is not performed with body size correction based on the low frequency gain, is used as the illness-related gain. As shown in FIG. 11, a significant correlation between R5 and the illness-related gain can be seen (correlation coefficient=0.485, significance probability<0.001). R5 represents total respiratory tract resistance of the entire lung, and it becomes harder for the patient to breathe as the value of R5 increases. As shown in FIG. 11, R5 and the illness-related gain have a positive correlation and therefore it is likely that the illness-related gain represents the state of the whole lung parenchyma that affects the total respiratory tract resistance, though it might be because the influence of the body size remains.

Here, the physiological sound examination device 100 can quantify the variation in the lung parenchyma caused by the illness with reducing the influence of the body size by using the illness-related gain that is resulted from calculating the ratio of the high frequency gain to the low frequency gain, instead of directly using the high frequency gain. For example, forming of edema on the lung parenchyma or consolidation of the lung parenchyma, caused by the illness, makes it easier for the lung sound to propagate. In this case, the value of the illness-related gain increases. When the illness-related gain is denoted by log, the illness-related gain is a negative number, and is closer to 0 dB as it becomes easier for the lung sound to propagate.

As described above, the physiological sound examination device 100 can evaluate the states of the respiratory tract and the lung parenchyma with reduced influence of the age, the body size, and the like and without requiring controlling the respiratory flow velocity, by using the illness-related high frequency power ratio and the illness-related gain.

Although the power ratio calculation unit 304 has directly calculated the ratio of the power spectrum in the step S701, the cross-spectral method may be used.

It is to be noted that in the step S701, the power calculation unit 301 may calculate the power only in each of the low frequency and the high frequency. In this case, the low frequency gain and the high frequency gain can be calculated if the power calculation unit 301 calculates the power in the low frequency and the high frequency, and the power ratio calculation unit 304 calculates the power ratio of the low frequency and the high frequency. As a result, there is no need to perform frequency conversion in all of the bands for calculating the power spectrum, whereby the computing amount can be reduced. It is to be noted that a bandpass filter may be designed for each frequency band so that the power of each frequency band is calculated.

Although the ratio of the high frequency gain to the low frequency gain has been calculated by the illness-related gain calculation unit 305, a low frequency gain reference value may be used instead of the low frequency gain. The low frequency gain reference value is a value which is calculated using the correction formula and at least one of physique parameter including the height, the age, the weight, the gender, the body surface area, and the body mass index. In this case, it is required to preliminarily record, in the recording unit 107, the correction formula for correcting the low frequency gain from the physique parameter. This makes it possible to calculate the low frequency gain associated with the body size with a higher degree of accuracy.

The time period for analysis of the lung sound performed by the physiological sound examination device 100 may be any one of (i) the whole or part of inspiration period, (ii) the whole or part of expiration period, and (iii) both or part of the inspiration period and the expiration period. In particular, the whole or part of the inspiration period is desirable. It is because the inspiration period has a characteristic that the lung sound can be measured in the chest at a high S/N ratio as compared with the expiration period.

Although it is described that each of the physiological sound measurement units 101 and 102 includes a lead wire 204 to transmit the physiological sound signal, the configuration is not limited to the above and may be a configuration in which the physiological sound signal is transmitted via a wireless communication instead of the lead wire 204. With this configuration, the lead wire 204 is not required. Accordingly, when measuring the physiological sound, noise can be prevented from being mixed to the physiological sound from the lead wire 204. The noise is caused by vibration of the lead wire 204 through contacting the body and by an electromagnetic wave or the like.

Although it is described that each of the physiological sound measurement units 101 and 102 detects the physiological sound using the microphone 203, an acceleration sensor may be used to detect the physiological sound. In this case, the diaphragm part 201 and the cavity part 202 are not required. As a result, the ambient noise that propagates through the air vibration can be prevented from being mixed into the sensor via the diaphragm part 201 and the cavity part 202.

[Embodiment 2]

What are described in the present embodiment are (i) a method of determining the state (good state or bad state) of the living body based on the illness-related high frequency power ratio and the illness-related gain which are calculated after the physiological sound is obtained in Embodiment 1 and (ii) a method of setting information that is used as the basis of the determination.

Figure 12:
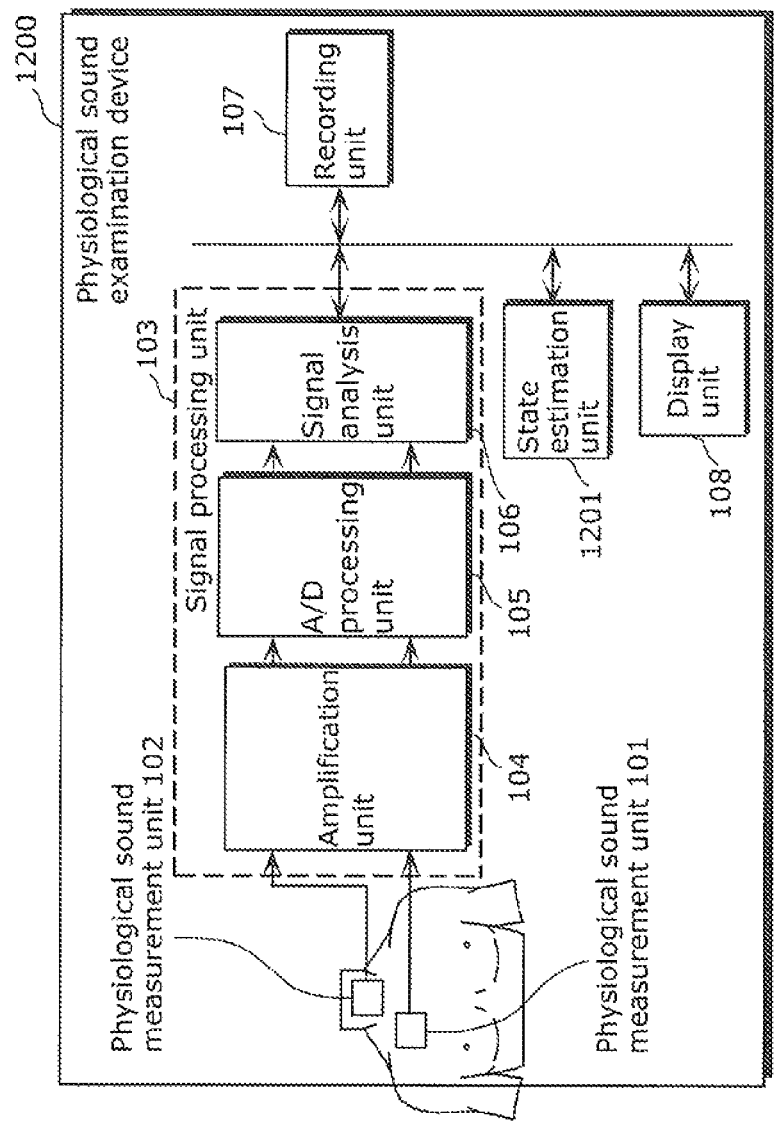
FIG. 12 shows an example of a functional block configuration of a physiological sound examination device according to Embodiment 2.

FIG. 12 shows an example of a functional block configuration of a physiological sound examination device 1200 according to Embodiment 2. The constituents which are the same as those in Embodiment 1 are designated by the same numerals and are not described.

As shown in FIG. 12, the physiological sound examination device 1200 includes a state estimation unit 1201 which identifies the state of the living body using the analysis result calculated by the signal analysis unit 106 and the identification information preliminarily recorded in the recording unit 107.

Figure 13:
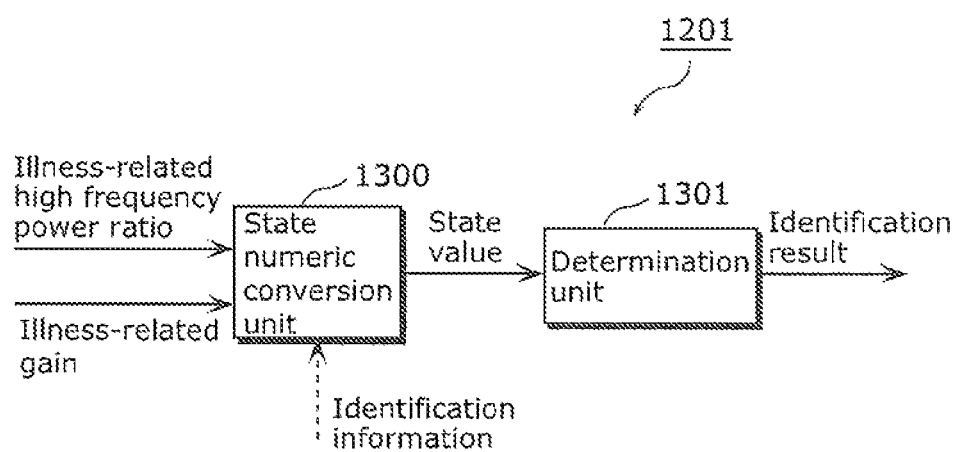
FIG. 13 shows an example of a functional block configuration of a state estimation unit.

FIG. 13 shows an example of a functional block configuration of the state estimation unit 1201. As shown in FIG. 13, the state estimation unit 1201 includes a state numeric conversion unit 1300 which numerically converts the state of the living body, and a determination unit 1301 which determines the state of the living body using the result obtained by the state numeric conversion unit 1300.

The following describes an operation performed by the physiological sound examination device 1200 when a physiological sound signal is inputted.

Figure 14:
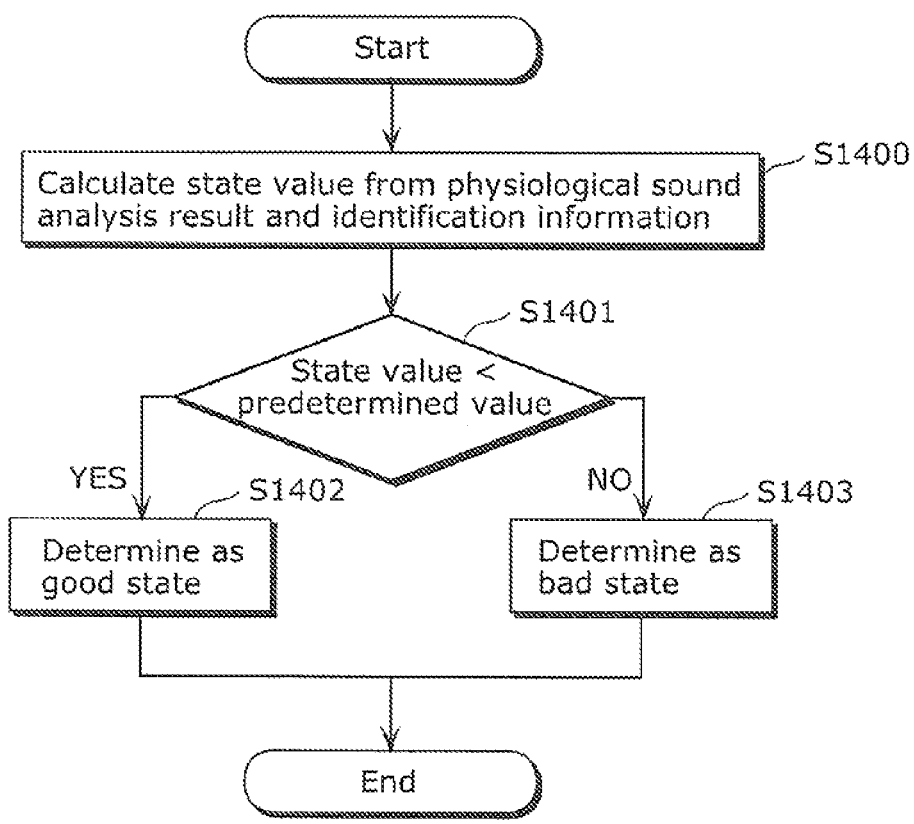
FIG. 14 is a flowchart showing an example of a method of estimating a state of a living body.

FIG. 14 is a flowchart showing an example of the method of estimating the state of the living body performed by the state estimation unit 1201.

First, the state numeric conversion unit 1300 calculates a state value indicating the state of the living body, using the illness-related high frequency power ratio and the illness-related gain calculated by the signal analysis unit 106, and the identification information preliminarily recorded in the recording unit 107 (step S1400).

Here, the identification information is a function for calculating a continuous value using the illness-related high frequency power ratio and the illness-related gain as shown in Equation 5, for example.

$$Z=0.273*DGain+0.351*DHiPow+4.124 \quad \text{(Equation 5)}$$

Here, Z represents a state value, DGain represents an illness-related gain, and DHiPow represents an illness-related high frequency power ratio. Equation 5 is an example obtained by en experiment, and another equation may be used.

The determination unit 1301 compares the state value calculated by the state numeric conversion unit 1300 and a predetermined value (step S1401). When the state value is smaller than the predetermined value, it is determined that the living body is in the good state (step S1402). Meanwhile, when the state value is greater than or equal to the predetermined value, it is determined that the living body is in the bad state (step S1403).

As a result, it is possible to determine the state of the living body from the two indexes which are the illness-related high frequency power ratio and the illness-related gain.

Figure 15:
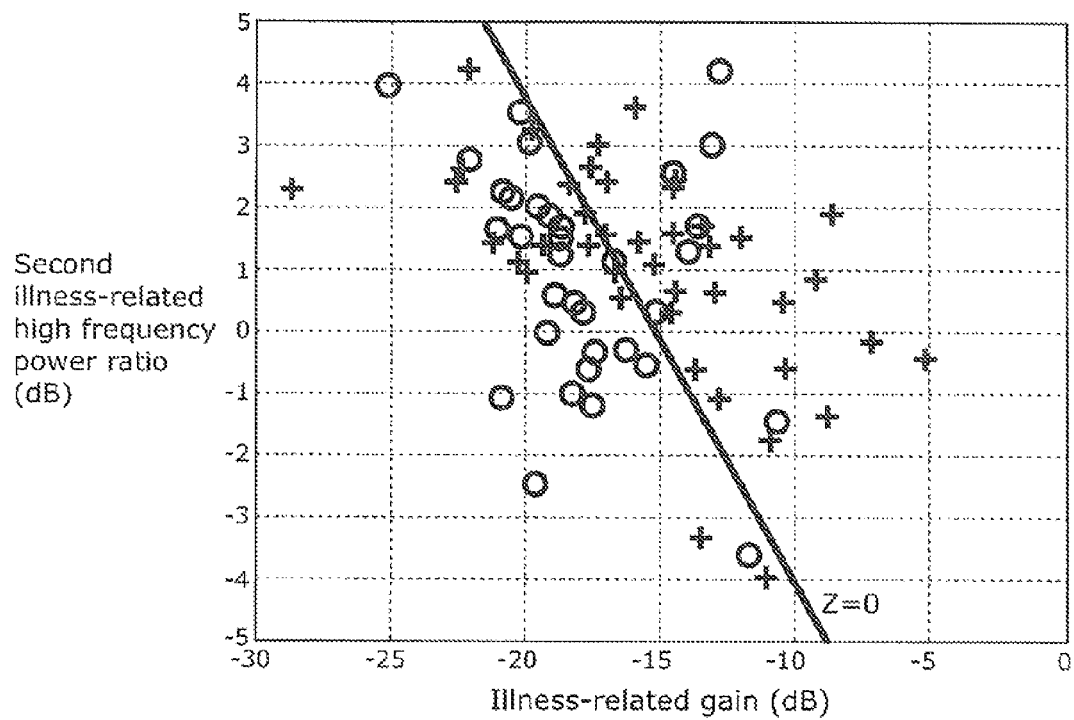
FIG. 15 is a scatter diagram showing an example of a relationship between the illness-related high frequency power ratio and an illness-related gain, of an asthma patient.

FIG. 15 is a scatter diagram showing an example of a relationship between the illness-related high frequency power ratio and the illness-related gain, of an asthma patient. In FIG. 15, a circle indicates a value obtained by an analysis of the lung sound measured when the patient has no symptom of asthma, including an attack or the like, that is an analysis value of the lung in the good state (good state). A plus indicates a value obtained by the analysis of the lung sound measured when the patient has a symptom of asthma, including an attack and cough, or when the patient is under an activity restriction, that is an analysis value of the lung in the bad state (bad state).

The solid line indicating Z=0 shown in FIG. 15 is a line on which a value of the discrimination function is 0. The discrimination function is obtained in order to determine with high accuracy two groups of analysis values including the analysis values of the lung in the good state and the analysis values of the lung in the bad state. The discrimination function to be used in this case is represented by Equation 5.

In Equation 5, the line indicating Z=0 serves as a border showing whether or not the two groups can be determined with higher accuracy. Therefore, it is desirable to set the predetermined value in the determination unit 1301 to "0" when the discrimination function represented by Equation 5 is used as the identification information. Another predetermined value may also be used depending on a purpose of use.

Furthermore, sensitivity and specificity in the examination can be changed by selectively increasing and decreasing the predetermined value. Here, the sensitivity represents a ratio of the number of living bodies determined being bad to the number of living bodies determined being truly bad. Meanwhile, the specificity represents a ratio of the number of living bodies determined being good to the number of living bodies determined being truly good.

That is, when the physiological sound examination device 1200 determines that a living body is in a bad state as a result of the measurement of the lung sound and it is preferred to enhance the sensitivity, it is appropriate to set the predetermined value to a value smaller than "0". Meanwhile, when the physiological sound examination device 1200 determines that a living body is in a good state and it is preferred to enhance the specificity, it is appropriate to set the predetermined value to a value greater than "0".

As described above, a desirable predetermined value varies depending on the purpose of use. Therefore, a configuration may be adopted in which the predetermined value can be arbitrarily changed by the operator of the physiological sound examination device.

It goes without saying that the appropriate setting of the predetermined value is also different depending on what equation is used as the discrimination function. It is sufficient that the equation and the predetermined value are appropriately set depending on each device of the apparatus or the environment so that whether the lung is in the good state or the bad state can be determined.

Figure 16:
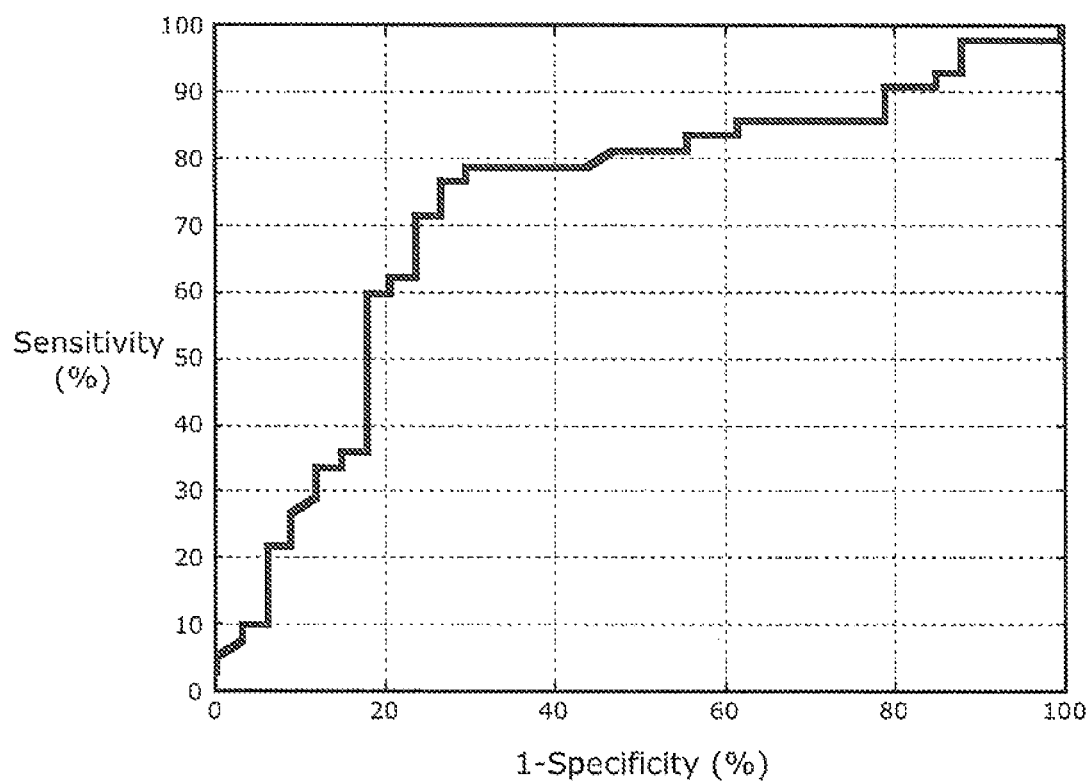
FIG. 16 shows an example of an ROC curve.

FIG. 16 shows an ROC curve when the predetermined value is changed using the discrimination function represented by Equation 5, in the scattering state in FIG. 15. Generally, an ROC curve represents the relationship between the sensitivity and the specificity when the predetermined value is changed, and one predetermined value corresponds to a point on the ROC curve. When the physiological sound examination device 1200 displays an ROC curve, the operator can grasp the relationship between the sensitivity and the specificity from the ROC curve, and change the predetermined value to a desirable value, thereby changing the purpose of use in the examination. Moreover, if the predetermined value corresponding to an arbitrary point on the ROC curve is preliminarily recorded in the recording unit 107 by the physiological sound examination device 1200, the operator can easily set the predetermined value to the desirable value by simply selecting the arbitrary point on the ROC curve.

Figure 17:
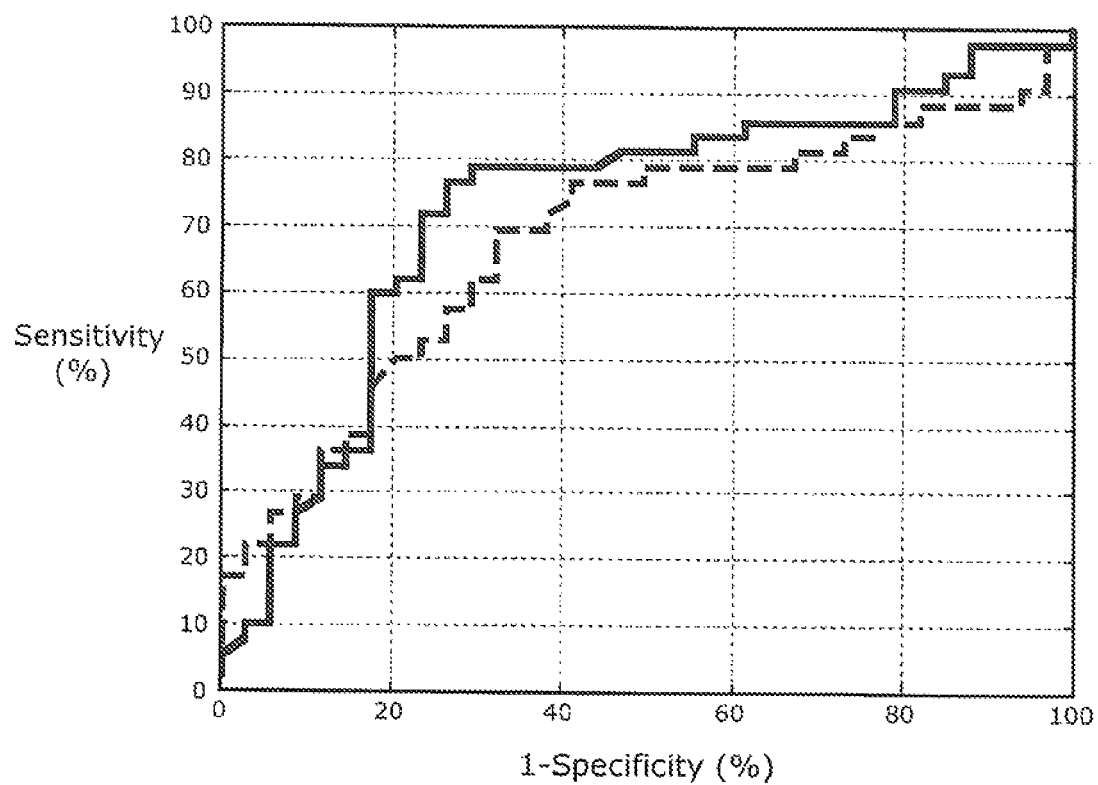
FIG. 17 shows another example of the ROC curve.

It is to be noted that FIG. 17 shows the ROC curve in FIG. 16, and an ROC curve obtained when the two groups in FIG. 15 are identified using only the illness-related gain (dotted line in FIG. 17). The ROC curve is closer to the upper left as both of the sensitivity and the specificity are higher. Accordingly, as it is clear from FIG. 17, the accuracy in identification is enhanced in the case where both of the indexes, including the illness-related gain and the illness-related high frequency power ratio, are used as compared to the case where only the illness-related gain is used.

Although an example using the discrimination function as the identification information is explained, another identification method may be used. For example, (i) a supervised classification such as Support Vector Machine (SVM), Neural Network, Gaussian Mixture Model (GMM), and K-means, (ii) an association rule such as a priori, and (iii) an unsupervised classification such as self-organizing map may be used, and a configuration may be adopted in which the identification information is changed depending on the purpose of use.

For example, different identification information may be used for the case where the physiological sound examination device 1200 is used for differential diagnosis of asthma or for follow-up during treatment. Furthermore, the identification information may be changed for each illness. With this configuration, the identification information and the predetermined value can be set for each purpose of use or illness, whereby the accuracy in identification can be enhanced.

It is to be noted that the identification information and the predetermined value may be changed depending on the medication information such as the type or amount of dosage.

It is to be noted that the determination results obtained in the steps S1402 and 51403 may be inverted depending on the type of the identification information, type of the illness associated with the determination result, or the purpose of use. That is, the living body may be determined as being in the bad state when the state value is smaller than the predetermined value in the step S1401, and as being in the good state when the state value is greater than or equal to the predetermined value.

It is to be noted that variation in the state of the living body caused by an illness varies depending on the difference among individuals and a treatment status such as dosage. Therefore, a configuration may be adopted in which a predetermined value for each individual is learned and the predetermined value is sequentially updated. For example, when the physiological sound of one person is periodically measured, (i) a correct answer label may be assigned for each measured value to indicate whether the value is of the good state or the bad state, based on the result obtained by other examination equipment or diagnosis by a the doctor and (ii) the physiological sound examination device 1200 may be caused to learn the identification information and the predetermined value, so that the identification on the good state and the bad state can be performed with higher accuracy based on the accumulated measured value and the correct answer label. With this configuration, appropriate identification information and the predetermined value can be set for each individual, whereby the accuracy in identification can be enhanced.

As the identification information, information other than the analysis result obtained by the signal analysis unit 106 may be used. The example includes the results obtained from examinations on blood pressure, body temperature, blood, lung function, exhaled NO, and IOS. The example further includes a result of a questionnaire to a patient regarding the illness, clinical end-point and physical findings determined by a doctor, case history and anamnestic history of the patient and the family, and medication information such as the type and amount of dosage. Moreover, the example includes: basic physical information of the patient, such as the height, the age, the weight, the gender, the body surface area, and the body mass index (BMI); whether information such as temperature, humidity, and air pressure; atmosphere information such as pollen scattering situation and air pollution situation; whether or not the patient exercises; activity information obtained by a pedometer or the like; and the time at which the state is worsened. With this configuration, the state can be estimated for the patient by identifying whether the patient is in the good state or the bad state, with taking the amount of characteristic that is specific to the case where the state is worsened, whereby the accuracy in identification can be enhanced.

For example, in the case of asthma, a cause for worsening the state is different form person to person. One is likely to have an attack due to exercising, while the other is likely to have an attack due to the change in air pressure. This is why combining the analysis result of the physiological sound with other information is effective in enhancing the accuracy in identification.

Although the two-dimensional map is divided into two areas by the discrimination function in the present embodiment, the two-dimensional map may be divided into plural, greater than or equal to three, according to the type of the illness or the meaning of each of the divided areas. The meaning of the area comes from, for example, a case where each area is associated with another area based on the value obtained by the spirometer or the exhaled NO measuring device. The two-dimensional map may be divided into three areas based on a combination of (i) whether the value obtained by the spirometer examination is good or bad and (ii) whether the value obtained by the exhaled NO examination is good or bad. The three areas include: an area A into which a patient with a bad value in both of the spirometer and the exhaled NO examinations is likely to be classified; an area B into which a patient with a good value in both of the spirometer and the exhaled NO examinations is likely to be classified; and an area C into which a patient with a bad value in one of the spirometer and the exhaled NO examinations is likely to be classified.

[Embodiment 3]

What is described in the present embodiment is a method of determining a shift in the state (good state or bad state) of the living body based on the illness-related high frequency power ratio and the illness-related gain which are calculated after the physiological sound is obtained in Embodiment 1.

Figure 18:
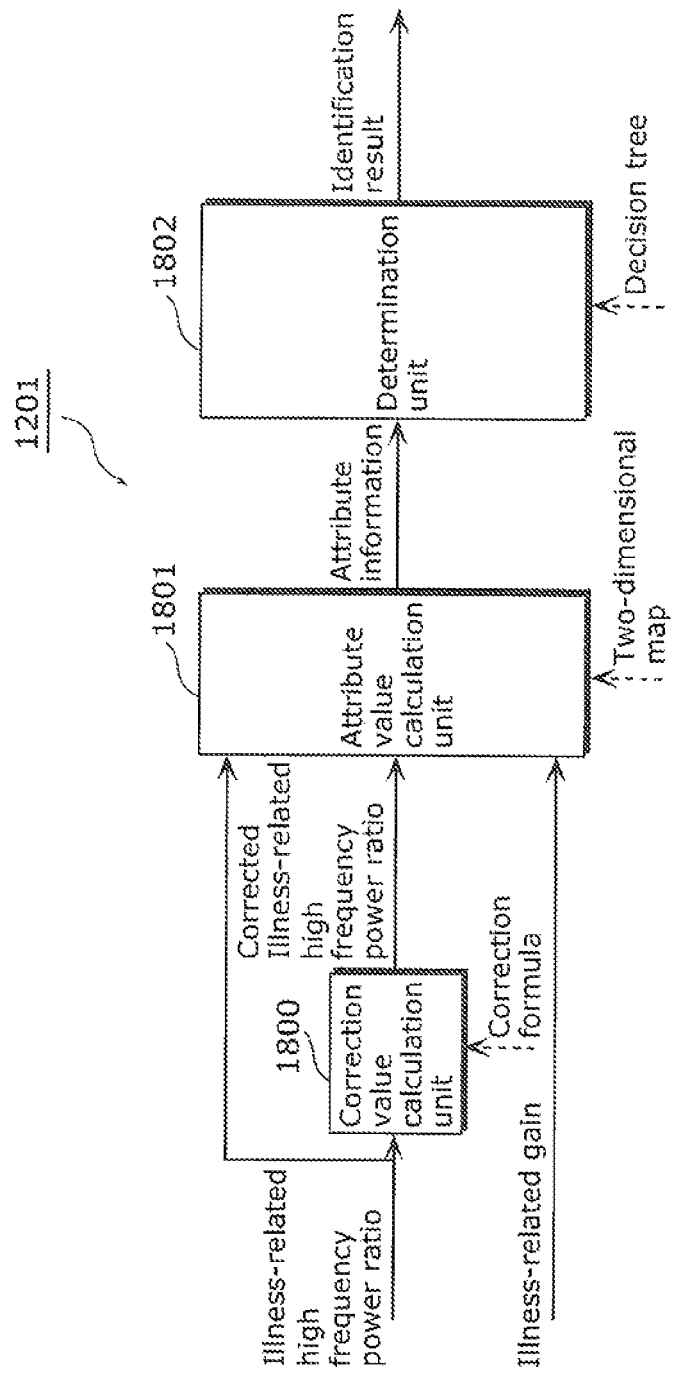
FIG. 18 shows another example of the functional block configuration of the state estimation unit.

FIG. 18 shows another example of the functional block configuration of the state estimation unit 1201 of the physiological sound examination device 1200 according to Embodiment 3. The constituents which are the same as those in Embodiment 2 are designated by the same numerals and are not described.

The state estimation unit 1201 includes: a correction value calculation unit 1800 which corrects the value of the illness-related high frequency power ratio; an attribute value calculation unit 1801; and a determination unit 1802 which determines the state of the living body from the attribute information.

Figure 19:
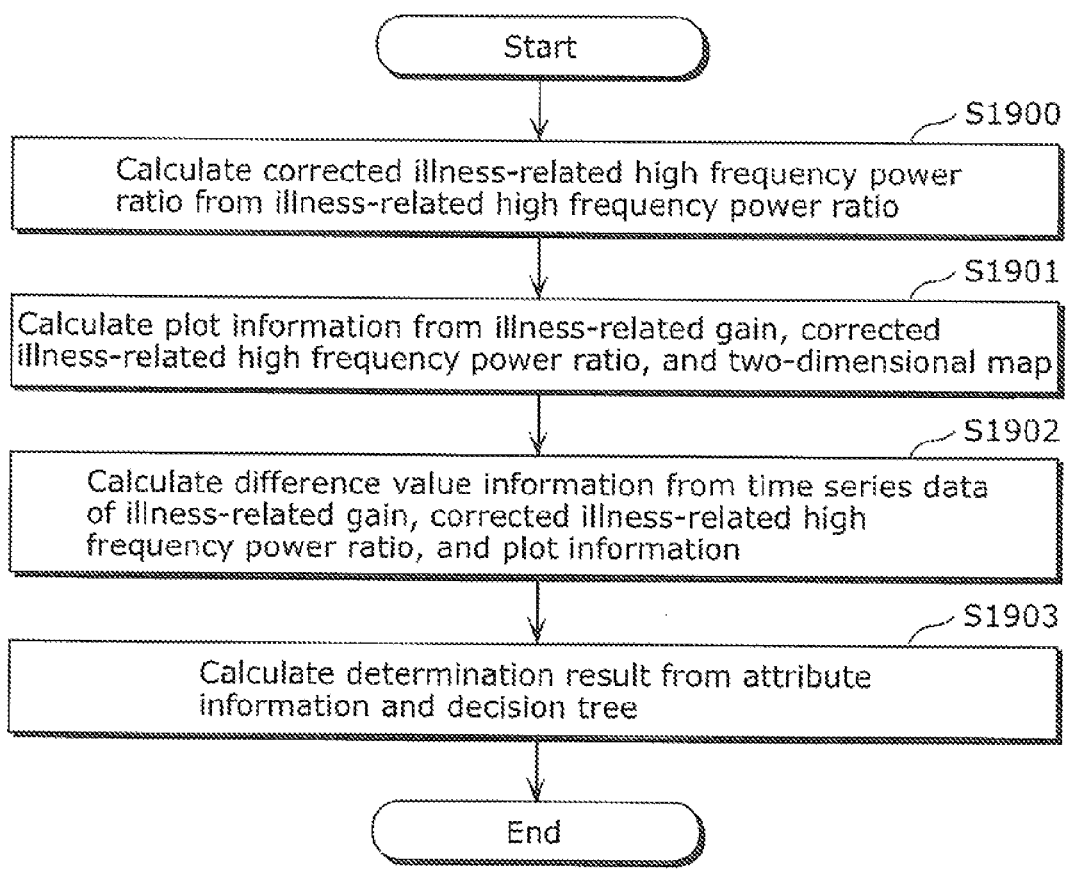
FIG. 19 is a flowchart showing another example of the method of estimating the state of the living body.

FIG. 19 is a flowchart showing another example of the method of estimating the state of the living body performed by the state estimation unit 1201.

The correction value calculation unit 1800 calculates a corrected illness-related high frequency power ratio using the illness-related high frequency power ratio and the illness-related gain calculated by the signal analysis unit 106, and for example, Equation 6 (step S1900).

$$CorDHiPow = DHiPow - (-0.184 * DGain - 3.003) \quad \text{(Equation 6)}$$

Here, CorDHiPow represents a corrected illness-related high frequency power ratio, and DGain represents the illness-related gain.

Figure 20:
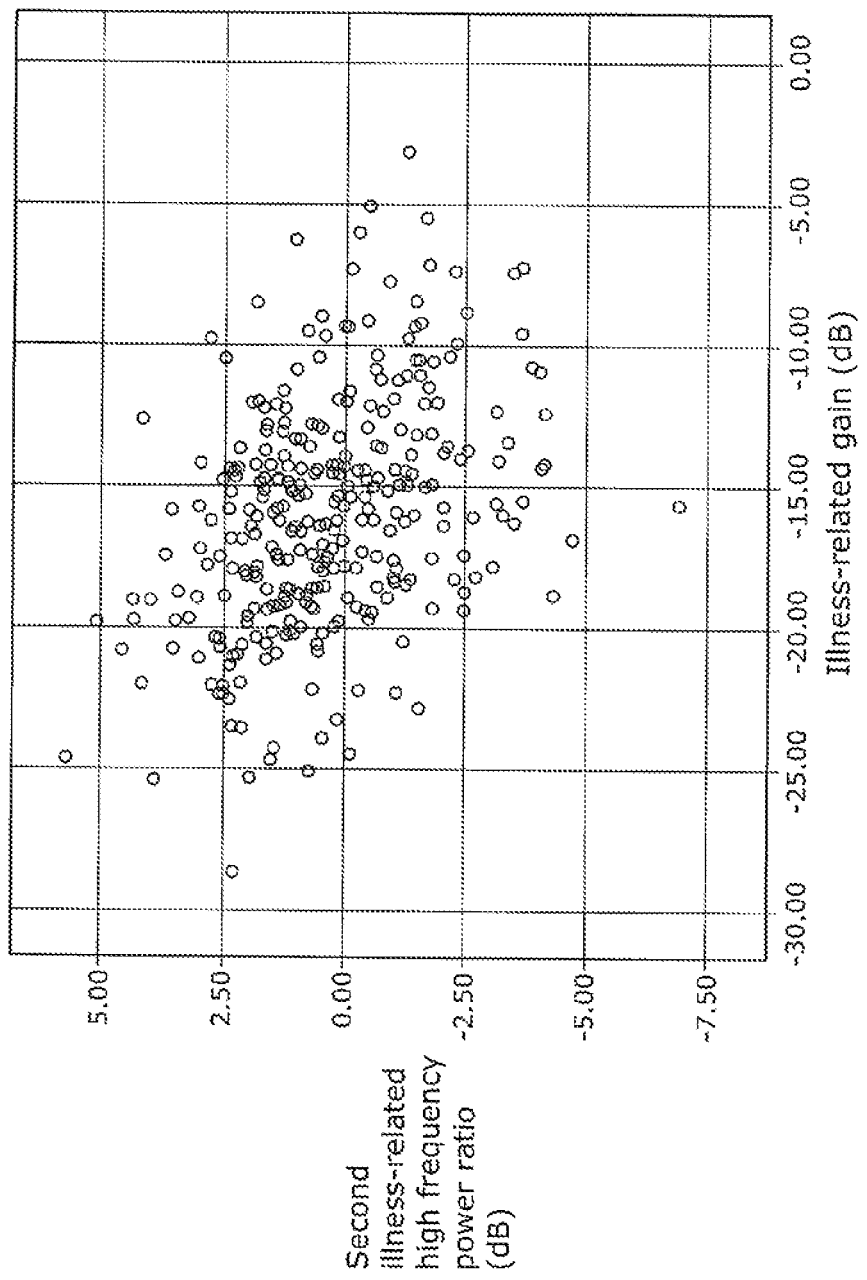
FIG. 20 is a scatter diagram showing another example of the relationship between the illness-related high frequency power ratio and the illness-related gain, of an asthma patient.

FIG. 20 is a scatter diagram showing another example of the relationship between the illness-related high frequency power ratio and the illness-related gain, of an asthma patient. As shown in FIG. 20, there is a negative correlation between the illness-related high frequency power ratio and the illness-related gain. Therefore, when the variation amount in the illness-related high frequency power ratio is analyzed, correction with the illness-related gain is required in some cases. Therefore, the correction with the illness-related gain is performed with Equation 6.

The second term on the right-hand side of Equation 6 (−0.184*DGain−3.003) represents a regression line that is calculated from the scatter diagram showing the relationship between the illness-related gain and the illness-related high frequency power ratio in the lung sound of an asthma patient with a mild state. With this regression line, an illness-related high frequency power ratio reference value for each illness-related gain of the lung that is relatively close to the normal state can be calculated.

The corrected illness-related high frequency power ratio represents the difference from the illness-related high frequency power ratio reference value. The state in a respiratory tract is worse. as this value is greater. Equation 6 is an example obtained by en experiment, and another equation may be used.

Next, the attribute value calculation unit 1801 calculates plot information in the two-dimensional map of the analysis value using the illness-related gain, the corrected illness-related high frequency power ratio, and the two-dimensional map recorded in the recording unit 107 (step S1901).

Figure 21:
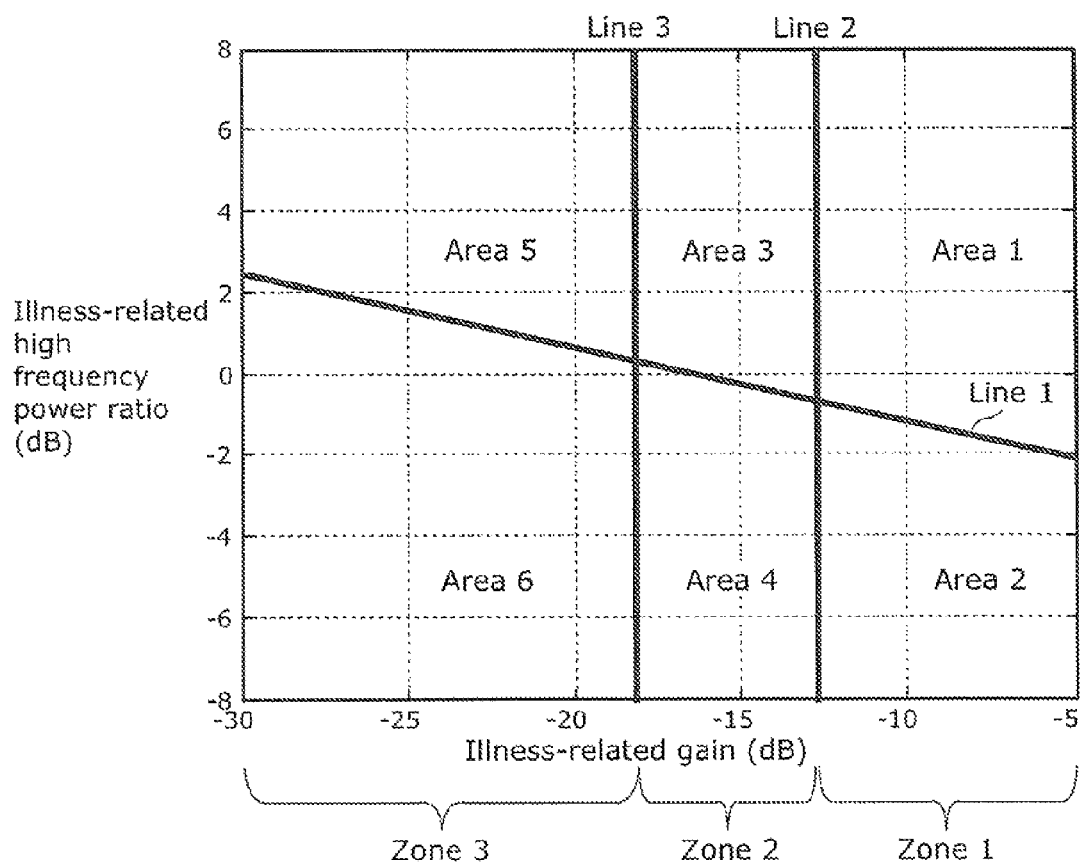
FIG. 21 shows an example of a two-dimensional map.

Here, the two-dimensional map is, for example, a map including information divided into plural areas and zones, in the graph including the horizontal axis for the illness-related gain and the vertical axis for the illness-related high frequency power ratio as shown in FIG. 21. Each area is assigned with an ordinal scale, and a value is assigned depending on the worsening of the state of the living body. The two-dimensional map shown in FIG. 21 is divided into six areas and three zones.

First, the area is described. The two-dimensional map is divided into plural areas by at least one of a line and a curve.

In FIG. 21, the graph area is divided into six areas by a line 1, a line 2, and a line 3. An area 1 includes the illness-related high frequency power ratio greater than or equal to the line 1 and the illness-related gain greater than or equal to the line 2. An area 2 includes the illness-related high frequency power ratio smaller than the line 1 and the illness-related gain greater than or equal to the line 2. An area 3 includes the illness-related high frequency power ratio greater than or equal to the line 1, and the illness-related gain smaller than the line 2 and greater than or equal to the line 3. An area 4 includes the illness-related high frequency power ratio smaller than the line 1, and the illness-related gain smaller than the line 2 and greater than or equal to the line 3. An area 5 includes the illness-related high frequency power ratio greater than or equal to the line 1 and the illness-related gain smaller than the line 3. An area 6 includes the illness-related high frequency power ratio smaller than the line 1 and the illness-related gain smaller than the line 3.

It is to be noted that an example of the line 1 in FIG. 21 is represented by Equation 7 that is the same as the second term on the right-hand side of Equation 6. Furthermore, an example of the line 2 is represented by Equation 5 by which a group of patients whose the lung sound is measured during an asthma attack and a group of patients other than the above can be identified with higher accuracy. An example of the line 3 is represented by Equation 6 by which lung sounds measured from a non-asthma patient and an asthma patient can be identified with higher accuracy.

$$DHiPow = -0.184 * DGain - 3.003 \quad \text{(Equation 7)}$$

$$DGain = -12.5 \quad \text{(Equation 8)}$$

$$DGain = -18.0 \quad \text{(Equation 9)}$$

Equation 7, Equation 8, and Equation 9 are obtained by an experiment, and other equations may be used.

Although the two-dimensional map in FIG. 21 is divided into six areas, it may be divided-into smaller than or equal to five areas by combining some of the areas. However, at least one of the area 1, area 2, and area 3, and at least one of the area 4, area 5, and area 6 may not be combined. It is because the analysis result of a patient having the bad state of asthma is often included in the area 1, area 2, and area 3, while the analysis result of a patient having the good state of asthma is often included in the area 4, area 5, and area 6. It is to be noted that the result of a patient who is likely to have an attack is often included in the area 1 and area 2. Therefore, an area resulting from combining the area 1 and area 2 may be the new area 1. Furthermore, the result of a patient having the good state of asthma is often included in the area 4 and area 5, and the result of a normal person is included in the area 6 relatively often. Therefore, an area resulting from combining the area 4 and area 5 may be the new area 4.

Next, the zone is described. The two-dimensional map is divided into plural zones in the direction of the axis for the illness-related gain.

In FIG. 21, a zone 1 includes the illness-related gain greater than or equal to the line 2. A zone 2 includes the illness-related gain smaller than the line 2 and greater than or equal to the line 3. A zone 3 includes the illness-related gain smaller than the line 3. In the zone 1, the analysis result of the patient who is likely to have an attack is often included. In the zone 2, the analysis result of the patient having relatively instable state, that is, the patient whose status is likely to vary in the good state and the bad state, is often included. In the zone 3, the analysis result of the patient having good and relatively stable state or a normal person is often included.

The plot information is at least one of an area number and a zone number which correspond to a point, in the two-dimensional map, plotted based on the illness-related gain and the illness-related high frequency power ratio. In FIG. 21, each of the area 1 to the area 6 is assigned with an area number and each of the zones 1 to the zone 3 is assigned with a zone number, in an ascending order starting from 1. However, without being limited to the above, any values may be used as long as the ordinal scale corresponding to the state of the living body in each area and zone can be distinguished.

The attribute value calculation unit 1801 calculates difference value information that is the variation amount from an immediately previous measured value to a current measured value of the illness-related gain, the corrected illness-related high frequency power ratio, and the plot information measured for one person at a different time (step S1902). The difference value information is not limited to the variation amount from the immediately previous measured value to the current measured value, but may be log information by which the history of variation is shown in time series, that is, the variation amount from a second previous measured value to the immediately previous measured value, and from the second previous measured value to a further previous measured value.

The determination unit 1802 performs a determination, based on a decision tree that is the identification information preliminarily recorded in the recording unit 107 (step S1903), using the attribute information including at least one of (i) the difference value information, (ii) the illness-related gain, the illness-related high frequency power ratio, and the corrected illness-related high frequency power ratio which are obtained from the current measurement and the plot information and (iii) the illness-related gain, the illness-related high frequency power ratio, and the corrected illness-related high frequency power ratio which are obtained from the immediately previous measurement and the plot information.

Figure 22:
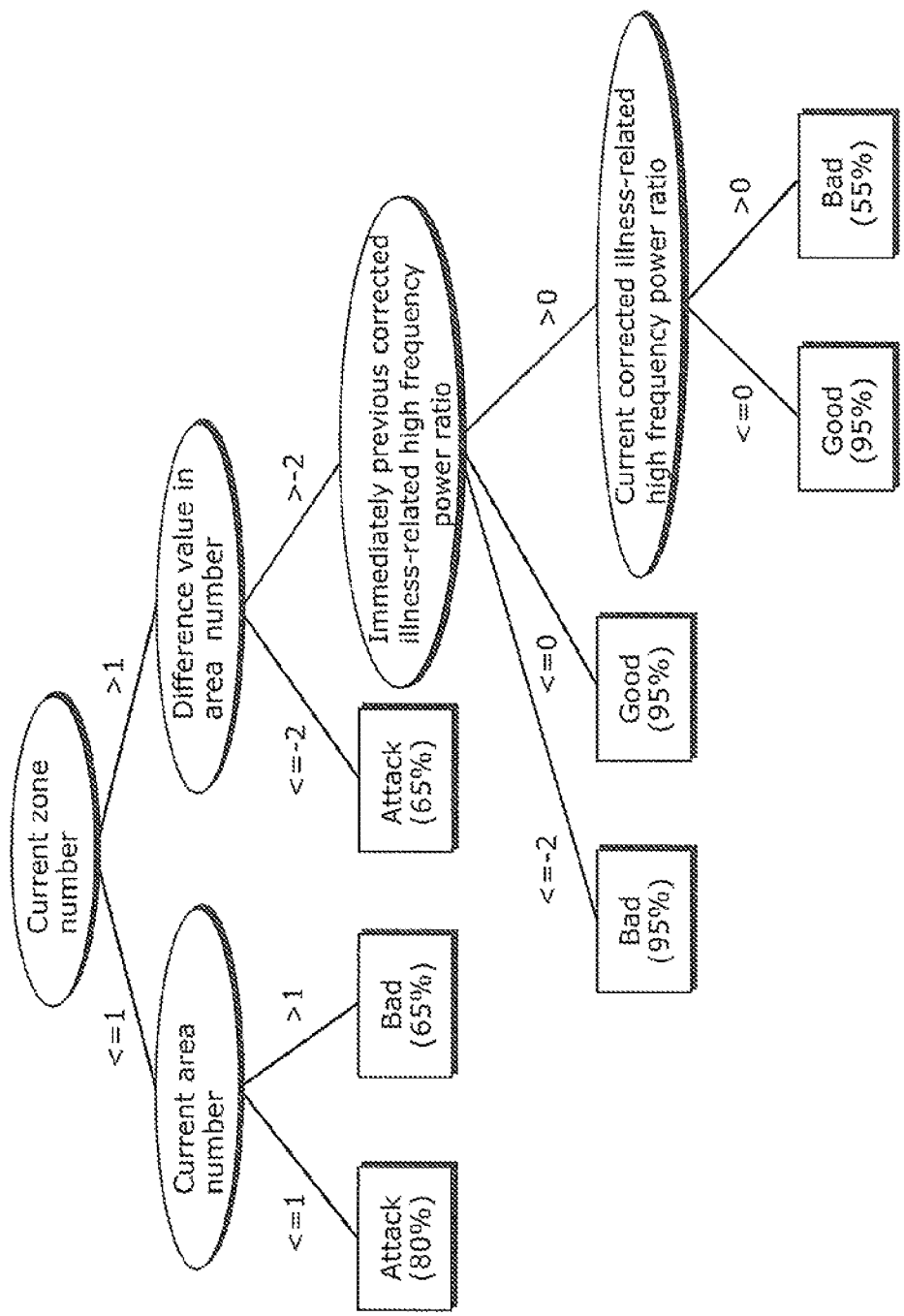
FIG. 22 shows an example of a decision tree.

FIG. 22 is an example of the decision tree. When the determination is performed using the decision tree shown in FIG. 22, the attribute information outputted from the attribute value calculation unit 1801 to the determination unit 1802 includes the plot information, the immediately-previous corrected illness-related high frequency power ratio, and the current corrected illness-related high frequency power ratio. Without being limited to the above, the attribute information is different depending on what kind of decision tree is used. Furthermore, the decision tree is changed depending on the race, the illness, the target age, and the purpose of use of the information to be identified.

The attribute information and the predetermined value, described in a circled position that is called a "node" in FIG. 22, are compared and the determination proceeds from the top to down based on the comparison result. The determination ends when the determination result is classified into a squared portion that is called a leaf. It helps the measurer understand the determination result if the determination result, degree of reliability, and determination reason corresponding to each leaf are set in advance and displayed with the determination result. In each leaf shown in FIG. 22, (i) the determination result out of attack, bad, and good and (ii) the degree of reliability (shown in percent) are described. Furthermore, the measurer can visually understand the variation in the state with ease if the two-dimensional map and the time-series analysis result of the subject are simultaneously displayed.

Figure 23:
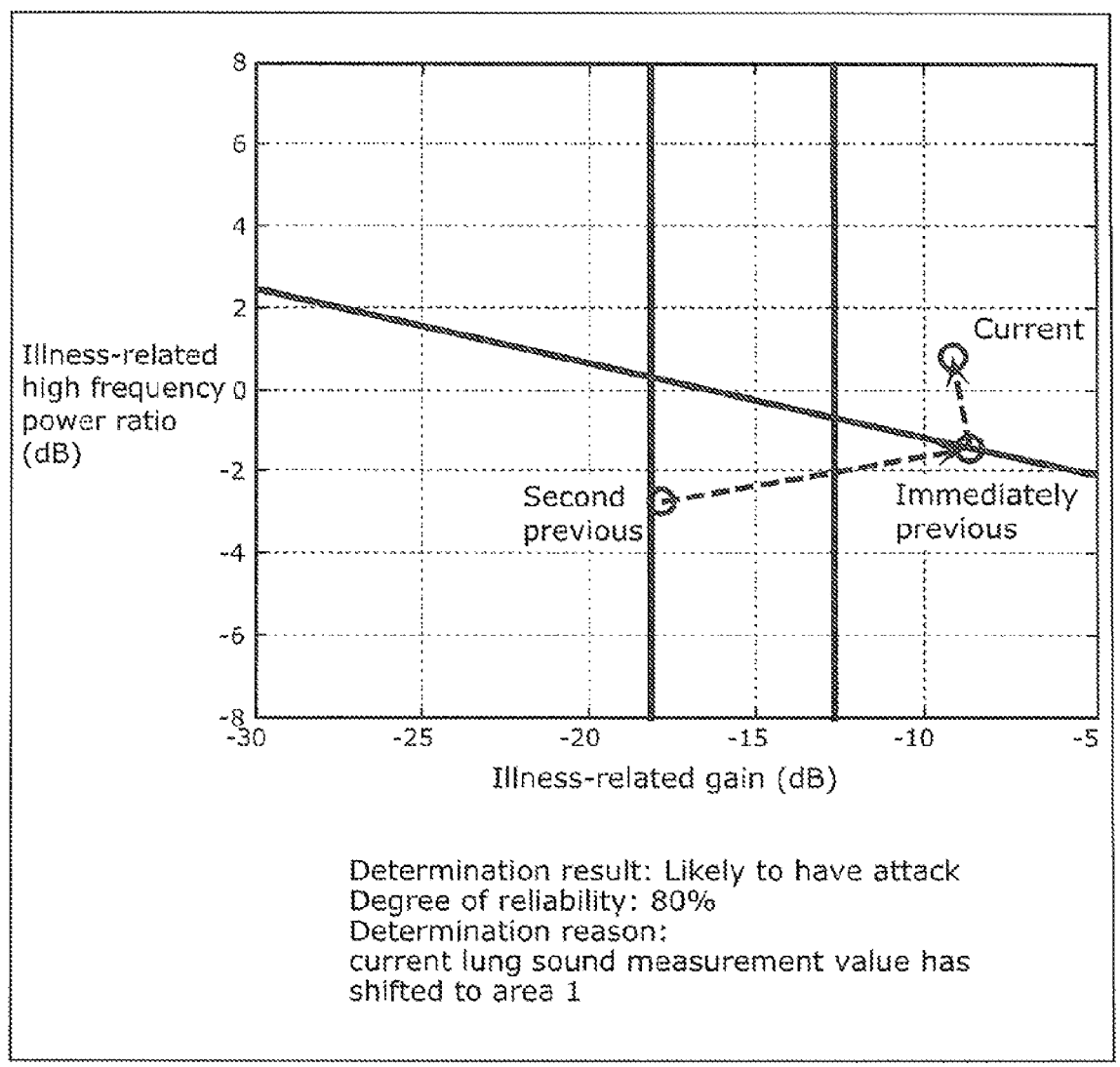
FIG. 23 shows an example of output display of the physiological sound examination device.

FIG. 23 shows an example of the output result. The graph in FIG. 23 shows, in the two-dimensional map, the results obtained from successive three, namely, the current, the immediately previous, and the second previous lung sound analyses.

Displaying the lung sound analysis result in a manner that the time series can be understood as described above makes it easier to visually understand the variation in the state of the lung. The two-dimensional map shows that the state is worse as the analysis result is closer to the upper right. Therefore, in the case shown in FIG. 23, it is easy to grasp that the state is gradually worsening because the diagnosis result obtained from the lung sound analysis has shifted in sequence from the area 4 to the area 2, and to the area 1, in the successive three lung sound analyses.

Furthermore, wording indicating the determination result determined using the identification information, such as the decision tree and the determination reason, may also be displayed so that it is easier for a third party to understand. As the degree of reliability, a degree of accuracy in classifying training data into each leaf, obtained when the physiological sound examination device 1200 has learned the decision tree using the training data, may be used. Also, the degree of accuracy in classifying, obtained when a determination capability test for the decision tree using test data was conducted, may be used. It goes without saying that the degree of reliability may be decided by other methods.

Although the decision tree is used in the above description, other identification information may be used. For example, (i) a supervised classification such as Support Vector Machine (SVM), Neural Network, Gaussian Mixture Model (GMM), and K-means, (ii) an association rule such as a priori, and (iii) an unsupervised classification such as self-organizing map may be used, and a configuration may be adopted in which the identification information is changed depending on the purpose of use.

It is to be noted that variation in the state of the living body caused by an illness varies depending on the difference among individuals and a treatment status such as dosage. Therefore, a configuration may be adopted in which a predetermined value for each individual is learned and the predetermined value is sequentially updated.

For example, when the physiological sound of one person is periodically measured, (i) a correct answer label may be assigned for each measured value to indicate whether the value is of the good state or the bad state of the lung, based on the result obtained by other examination equipment or diagnosis by a doctor and (ii) the physiological sound examination device 1200 may be caused to learn the identification information and the predetermined value, so that the identification on the good state and the bad state of the lung can be performed with higher accuracy based on the accumulated measured value and the correct answer label. With this configuration, appropriate identification information and the predetermined value can be set for each individual, whereby the accuracy in identification can be enhanced.

As the identification information, information other than the analysis result obtained by the signal analysis unit 106 may be used. The example includes the results obtained from examinations on blood pressure, body temperature, blood, lung function, exhaled NO, and IOS. The example further includes a result of a questionnaire to a patient regarding the illness, clinical end-point and physical findings determined by a doctor, and case history and anamnestic history of the patient and the family. Moreover, the example includes: basic physical information of the patient, such as the height, the age, the weight, the gender, the body surface area, and the body mass index (BMI); whether information such as temperature, humidity, and air pressure; atmosphere information such as pollen scattering situation and air pollution situation; whether or not the patient exercises; activity information obtained by a pedometer or the like; and the time at which the state is worsened. With this configuration, the state can be estimated for the patient by identifying whether the patient is in the good state or the bad state, with taking the amount of characteristic that is specific to the case where the state is worsened, whereby the accuracy in identification can be enhanced.

For example, in the case of asthma, a cause for worsening the state is different form person to person. One is likely to have an attack due to exercising, while the other is likely to have an attack due to the change in air pressure. This is why combining the analysis result of the physiological sound with other information is effective in enhancing the accuracy in identification.

It is to be noted that the six areas shown in FIG. 21 are an example of division, and the two-dimensional map may be divided into more areas or divided by another method, according to the type of the illness or the meaning of each areas. The meaning of each area comes from, for example, a case where each area is associated with another area based on the value obtained by the spirometer or the exhaled NO measuring device. The two-dimensional map may be divided into three areas based on a combination of (i) whether the value obtained by the spirometer examination is good or bad and (ii) whether the value obtained by the exhaled NO examination is good or bad. The three areas include: an area A into which a patient with a bad value in both of the spirometer and the exhaled NO examinations is likely to be classified; an area B into which a patient with a good value in both of the spirometer and the exhaled NO examinations is likely to be classified; and an area C into which a patient with a bad value in one of the spirometer and the exhaled NO examinations is likely to be classified.

[Other Modifications]

Although the present invention has been described thus far based on the embodiments, the present invention is not determined by the embodiments. The present invention further includes the following cases.

(1) Some or all of the components included in each of the above-described devices may be a computer system including a microprocessor, a ROM (Read Only Memory), a RAM (Random Access Memory), and a hard disk unit. The RAM or the hard disk unit stores a computer program implementing the same operation as performed by the corresponding above-described device. The microprocessor operates according to the computer program, so that function of the corresponding above-described device is carried out.

(2) Some or all of the components included in each of the above-described devices may be realized as a single system LSI (Large Scale Integration). The system LSI is a super multifunctional LSI manufactured by integrating a plurality of components onto a signal chip. To be more specific, the system LSI is a computer system including a microprocessor, a ROM, and a RAM. The RAM stores a computer program implementing the same operation as performed by the corresponding above-described device. The microprocessor operates according to the computer program, so that a function of the system LSI is carried out.

(3) Some or all of the components included in each of the above-described devices may be implemented as an IC card or a standalone module that can be inserted into and removed from the corresponding device. The IC card or the module is a computer system including a microprocessor, a ROM, and a RAM. The IC card or the module may include the aforementioned super multifunctional LSI. The microprocessor operates according to the computer program, so that a function of the IC card or the module is carried out. The IC card or the module may be tamper resistant.

(4) The present invention may be methods implemented by the computer processing described above. Each of the methods may be a computer program implemented by a computer, or may be a digital signal of the computer program.

Moreover, the present invention may be the aforementioned computer program or digital signal recorded on a computer-readable recording medium. As the computer-readable recording medium, a flexible disk, a hard disk, a CD-ROM, an MO, a DVD, a DVD-ROM, a DVD-RAM, a BD (Blu-ray Disc), or a semiconductor memory can be used. Also, the present invention may be the digital signal recorded on such a recording medium.

Furthermore, the present invention may be the aforementioned computer program or digital signal transmitted via a telecommunication line, a wireless or wired communication line, a network represented by the Internet, or data broadcasting.

Moreover, the present invention may be a computer system including a microprocessor and a memory. The memory may store the aforementioned computer program and the microprocessor may operate according to the computer program.

Furthermore, by transferring the recording medium having the aforementioned program or digital signal recorded thereon or by transferring the aforementioned program or digital signal via the aforementioned network or the like, the present invention may be implemented by a different independent computer system.

(5) Moreover, the above embodiments and modifications may be combined.

As described above, the physiological sound examination device and the method thereof according to the present invention have advantageous effects of easily quantifying a state of a respiratory tract and a state of lung parenchyma simultaneously, by measuring lung sound, without requiring correction based on an age, a height, or the like nor control of the breathing, and are therefore effective in state estimation and the like of lungs with an illness and the like.

REFERENCE SIGNS LIST 100, 1200 Physiological sound examination device
101, 102 Physiological sound measurement unit
103 Signal processing unit
104 Amplification unit
105 A/D processing unit
106 Signal analysis unit
107 Recording unit
108 Display unit
201 Diaphragm part
202 Cavity part
203 Microphone
204 Lead wire
205 Filled part
301 Power calculation unit
302, 312 Reference power calculation unit
303 Illness-related high frequency power ratio calculation unit
304 Power ratio calculation unit
305 Illness-related gain calculation unit
306 Correction unit
1201 State estimation unit
1300 State numeric conversion unit.
1301, 1802 Determination unit
1800 Correction value calculation unit 1801 Attribute value calculation unit

The invention claimed is:

1. A physiological sound examination device which supports estimation of a state of a living body by measuring a physiological sound which propagates through the living body and calculating a plurality of physiological sound characteristics, the physiological sound examination device comprising:

a hardware processor, wherein the hardware processor is configured to:

calculate a power ratio which is a ratio of power of a first physiological sound signal to power of a second physiological sound signal, the first physiological sound signal being generated from a first physiological sound in a first portion of the living body and the second physiological sound signal being generated from a second physiological sound in a second portion of the living body;

calculate, as one of the physiological sound characteristics, a transfer characteristic index of the physiological sound in the living body by performing a computation on the power ratio so that an influence of at least one of a respiratory flow velocity of the living body and a size of the living body is reduced;

calculate first power which is power of the second physiological sound in a first frequency band: and calculate, as another one of the physiological sound characteristics, a sound source characteristic index of the physiological sound by performing a computation on the first power so that an influence of at least one of the respiratory flow velocity of the living body and the size of the living body is reduced.

2. The physiological sound examination device according to claim 1, wherein the hardware processor is configured to:

calculate second power which is power of the second physiological sound signal in a second frequency band which is different from the first frequency band, calculate a first power reference value that is a value obtained by reducing the influence of difference in sizes of the living bodies included in the second power, and perform the computation by calculating a ratio of the first power to the first power reference value, to calculate the sound source characteristic index.

3. The physiological sound examination device according to claim 2, wherein the second frequency band includes a frequency lower than a frequency in the first frequency band.

4. The physiological sound examination device according to claim 1, wherein the hardware processor is configured to:

calculate the power ratio in a third frequency band and the power ratio in a fourth frequency band which includes a frequency lower than a frequency in the third frequency band, and calculate, as the transfer characteristic index, a ratio of the power ratio in the third frequency band to the power ratio in the fourth frequency band.

5. The physiological sound examination device according to claim 1, wherein the hardware processor is configured to: calculate the power ratio in the third frequency band, and calculate a gain reference value, and calculate a ratio of the power ratio in the third frequency band to the gain reference value as the transfer characteristic index, the gain reference value being calculated using (i) at least one of a height, an age, a weight, a gender, a body surface area, and a body mass index, of the living body and (ii) a first gain prediction formula that is set in advance.

6. The physiological sound examination device according to claim 1, wherein the hardware processor is further configured to correct the sound source characteristic index based on at least one of a height, an age, a weight, a gender, a body surface area, and a body mass index, of the living body.

7. The physiological sound examination device according to claim 1, wherein the hardware processor is further configured to estimate whether the living body is in a good state or a bad state based on identification information set in advance, the calculated sound source characteristic index, and the calculated transfer characteristic index.

8. The physiological sound examination device according to claim 7, wherein the hardware processor is further configured to perform, using a discrimination function as the identification information, the estimation in which the living body is estimated to be in one of the good state and the bad state when a value of the discrimination function is greater than or equal to a predetermined value, and the living body is estimated to be in the other of the good state and the bad state when the value of the discrimination function is smaller than the predetermined value, when the sound source characteristic index and the transfer characteristic index are substituted into the discrimination function.

9. The physiological sound examination device according to claim 8, wherein the hardware processor is further configured to change a sensitivity and a specificity by selectively increasing and decreasing the predetermined value, the sensitivity being a rate that a living body truly in the bad state is determined to be in the bad state, and the specificity being a rate that a living body truly in the good state is determined to be in the good state, in the estimation.

10. The physiological sound examination device according to claim 7, wherein the hardware processor is further configured to estimate the state of the living body using a support vector machine as the identification information.

11. The physiological sound examination device according to claim 7, wherein the hardware processor is further configured to estimate the state of the living body from medication information related to medication for the living body.

12. The physiological sound examination device according to claim 1, further comprising a display configured to display an examination result including a two-dimensional map having two axes, one of the axes indicating the sound source characteristic index and the other of the axes indicating the transfer characteristic index, wherein the two-dimensional map is divided into a plurality of areas by at least one border line.

13. The physiological sound examination device according to claim 12, wherein the two-dimensional map is divided into three by lines or curves in a direction of the axis indicating the transfer characteristic index, and into two by at least one of a line and a curve in a direction of the axis indicating the sound source characteristic index.

14. The physiological sound examination device according to claim 12, wherein the hardware processor is further configured to perform estimation on whether the living body is in a good state or a bad state based on identification information set in advance, a measured sound source characteristic index, and a measured transfer characteristic index, wherein the estimation is performed using the border line as the identification information and based on the area, in the two-dimensional map, including coordinates corresponding to a calculated sound source characteristic index and a calculated transfer characteristic index.

15. The physiological sound examination device according to claim 14, wherein the hardware processor is further configured to estimate the state of the living body from (i) an area including the coordinates corresponding to the transfer characteristic index and the sound source characteristic index at a first time and (ii) an area including the coordinates corresponding to the transfer characteristic index and the sound source characteristic index at a second time that is different from the first time.

16. The physiological sound examination device according to claim 1, wherein the state of a living body is the state of asthmatic lungs.

17. The physiological sound examination device according to claim 1, further comprising:

a first physiological sound measurement device configured to measure the first physiological sound and generate the first physiological sound signal; and a second physiological sound measurement device configured to measure the second physiological sound and generate the second physiological sound signal, the second portion being closer to a sound source of the physiological sound than the first portion.

18. The physiological sound examination device according to claim 17, wherein the second portion is a predetermined portion in a chest or a neck, and the first portion is a predetermined portion in the chest.

19. The physiological sound examination device according to claim 18, wherein the first portion is at a sternal notch and the second portion is at a second intercostal space on a right midclavicular line.

20. The physiological sound examination device according to claim 18, wherein the second portion is closed to the neck than the first portion.

21. A physiological sound examination method of supporting estimation of a state of a living body by measuring a physiological sound which propagates through the living body and calculating a plurality of physiological sound characteristics, the physiological sound examination method comprising:

calculating a power ratio which is a ratio of power of the first physiological sound signal to power of the second physiological sound signal, the first physiological sound signal being generated from a first physiological sound in a first portion of the living body and the second physiological sound signal being generated from a second physiological sound in a second portion of the living body;

calculating, as one of the physiological sound characteristics, a transfer characteristic index of the physiological sound in the living body by performing a computation on the power ratio so that an influence of at least one of a respiratory flow velocity of the living body and a size of the living body is reduced;

calculating first power which is power of the second physiological sound signal in a first frequency band; and calculating, as another one of the physiological sound characteristics, a sound source characteristic index of the physiological sound by performing a computation on the first power so that an influence of at least one of the respiratory flow velocity of the living body and the size of the living body is reduced.

22. A non-transitory computer-readable recording medium for causing a computer to execute the physiological sound examination method according to claim 21.

* * * * *